United States Patent
Lutz et al.

(10) Patent No.: US 9,598,412 B2
(45) Date of Patent: Mar. 21, 2017

(54) SPIROINDOLINE COMPOUNDS FOR USE AS ANTHELMINTHICS

(71) Applicant: Intervet, Inc., Madison, NJ (US)

(72) Inventors: Jürgen Lutz, Schwabenheim (DE); Sandra Koch, Schwabenheim (DE); Manfred Uphoff, Schwabenheim (DE); Anja Regina Heckeroth, Schwabenheim (DE); Britta von Oepen, Schwabenheim (DE); Ulrich Sondern, Schwabenheim (DE); Christophe Pierre Alain Chassaing, Schwabenheim (DE)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/513,929

(22) Filed: Oct. 14, 2014

(65) Prior Publication Data

US 2015/0057302 A1    Feb. 26, 2015

Related U.S. Application Data

(62) Division of application No. 13/574,900, filed as application No. PCT/EP2011/051639 on Feb. 4, 2011, now abandoned.

(60) Provisional application No. 61/302,312, filed on Feb. 8, 2010.

(30) Foreign Application Priority Data

Feb. 5, 2010 (EP) ..................... 10152817

(51) Int. Cl.
| | |
|---|---|
| *A61K 31/438* | (2006.01) |
| *C07D 471/10* | (2006.01) |
| *A61K 31/444* | (2006.01) |
| *A61K 45/06* | (2006.01) |

(52) U.S. Cl.
CPC .......... *C07D 471/10* (2013.01); *A61K 31/438* (2013.01); *A61K 31/444* (2013.01); *A61K 45/06* (2013.01)

(58) Field of Classification Search
CPC ............................ C07D 471/10; A61K 31/438
USPC .............................................. 546/17; 514/278
See application file for complete search history.

(56) References Cited

U.S. PATENT DOCUMENTS 8,309,567 B2 * 11/2012 Cassayre et al. ............. 514/278

FOREIGN PATENT DOCUMENTS

| WO | 9429309 A1 | 12/1994 |
|---|---|---|
| WO | 9825605 A1 | 6/1998 |
| WO | 9828297 A1 | 7/1998 |
| WO | 9964002 A1 | 12/1999 |
| WO | 03106457 A1 | 12/2003 |
| WO | 2004035591 A1 | 4/2004 |
| WO | 2005-058897 | * 6/2005 |

OTHER PUBLICATIONS

European Search Report for Application No. 10152817.2, dated Nov. 16, 2010, 7 pages.
International Search Report for corresponding PCT Application No. PCT/EP2011/051639, mailed on Mar. 7, 2011, 4 pages.
Jabbar, et al., "Anthelmintic resistance: The state of play revisited", Life Sciences, 2006, pp. 2413-2431, vol. 79.
McKellar, et al., "Veterinary anthelmintics: old and new", Trends in Parasitology, 2004, pp. 456-461, vol. 20(10).

* cited by examiner

*Primary Examiner* — Rita Desai

(57) ABSTRACT

This invention relates to spiroindoline compounds for the treatment of helminth infections and the treatment of parasitosis, such as caused by helminth infections. This invention also relates to uses of the compounds to make medicaments and treatments comprising the administration of the compounds to animals in need of the treatments. Moreover this invention relates to pharmaceutical compositions and kits comprising the compounds.

8 Claims, No Drawings

SPIROINDOLINE COMPOUNDS FOR USE AS ANTHELMINTHICS

CROSS-REFERENCE TO RELATED APPLICATIONS

This application is a divisional application of U.S. application Ser. No. 13/574,900, filed on Jul. 24, 2012, which is a national stage entry under 35 U.S.C. §371 of PCT/EP2011/051639, filed on Feb. 4, 2011, which claims priority to U.S. Provisional Application No. 61/302,312, filed on Feb. 8, 2010, and EP Application No. 10152817.2, filed on Feb. 5, 2010. The content of PCT/EP2011/051639 is hereby incorporated by reference in its entirety.

FIELD OF THE INVENTION

This invention relates to certain spiroindoline compounds that are useful as medicaments, more specifically as medicaments for non-human animals. The medicament can preferably be used for the treatment of parasitic infections such as helminth infections and especially for the treatment of parasitoses, such as caused by helminth infections. This invention also relates to uses of the compounds to make medicaments and treatments comprising the administration of the compounds to animals in need of the treatments. This invention also relates to novel spiroindoline compounds and the preparation of said compounds. Moreover this invention relates to pharmaceutical compositions and kits comprising the compounds.

BACKGROUND OF THE INVENTION

Parasitic diseases in animals cause substantial suffering and economic losses throughout the world. Thus, treatment of parasitic infections remains an important global endeavor. The causative organisms include helminths, such as nematodes, cestodes, and trematodes. These organisms can infect, for example, the stomach, intestinal tract, lymphatic system, muscle tissues, kidney, liver, lungs, heart, and brain of animals.

There are many known drugs (or "anthelmintic agents") available to treat various helminith parasite infections, see, e.g., McKellar, Q. A., et al., "Veterinary anthelmintics: old and new," *Review: Trends in Parasitology*, 20(10), 456-61 (October 2004). These anthelmintic agents treat specifically either nematode or trematode infections or have a broader anthelmintic spectrum. An example of an anthelmintic agent with sole effect on cestodes (tapeworms) is praziquantel. Some primary nematicidal compounds like fenbendazole, mebendazole, oxfendazole, albendazole have a broader spectrum than nematodes and treat cestode infections as well. Closantel, rafoxanide and triclabendazole are examples of specific compounds for the treatment of trematode infections (flukes).

While many parasitic infections can be treated with known drugs, evolutionary development of resistance by the parasites can render such drugs obsolete over time, see, e.g., Jabbar, A., et al., "Anthelmintic resistance: the state of play revisited," *Life Sciences*, 79, 2413-31 (2006). In addition, known drugs may have other deficiencies, such as limited spectrum of activity and the need for repeated treatments.

In WO 94/29309 and WO 98/28297 spiro-substituted azacyclic compounds are disclosed which are useful as neurokinin antagonists. In WO 98/25605 and WO 99/64002 spiro-substituted azacyclic compounds are disclosed which are useful as modulators of chemokinine receptor activity and melanocortin receptor agonists respectively. In WO 03/106457, A1 spiroindoline derivatives with insecticidal properties are disclosed.

There still exists a need for new medicaments, such as antiparasitic agents to ensure safe, effective, and convenient treatment of a wide range of parasitic helminth infections over a long period of time.

SUMMARY OF THE INVENTION

Surprisingly it has been found that certain spiroindoline compounds can be used as medicaments, especially as antiparasitic agents such as anthelmintic agents.

Briefly, this invention relates to compounds that can generally be used as a medicament for animals. The compounds correspond in structure to formula (I)

(I)

wherein
Y=O, S;
Q=—$CH_2$—CH($CH_3$)—, —$CH_2$—$CH_2$—O—, —$CH_2$—$CH_2$—$CH_2$—O—, —$CH_2$—$CH_2$—$CH_2$—$CH_2$—O—, —$CH_2$—CH=CH—, —$CH_2$—$CH_2$—$CH_2$—;
$R^1$=H, F, Cl, $CH_3$, $OCH_3$, $CF_3$;
$R^2$=H, F, Cl, $CH_3$, $OCH_3$, $CF_3$;
$A^1$=H, halogen, $C_1$-$C_4$-alkyl;
$A^2$=H, halogen, $C_1$-$C_4$-alkyl, $C_1$-$C_4$-alkoxy, $C_1$-$C_4$-alkylthio, wherein $C_1$-$C_4$-alkyl, $C_1$-$C_4$-alkoxy and $C_1$-$C_4$-alkylthio are optionally perfluorinated such as $CF_3$, $OCF_3$, $SCF_3$;
$A^3$=H, halogen, $C_1$-$C_4$-alkyl;
$A^4$=H, halogen, $C_1$-$C_1$-alkyl;
$B^1$=H, F, Cl, $CH_3$, $CF_3$;
$B^2$=H, F, Cl, $CH_3$, $CF_3$, $NO_2$;
$B^3$=H, F, Cl, $CH_3$, $CF_3$, CN, $OCH_3$, $OCF_3$;
$B^4$=H, F, Cl, $CH_3$, $CF_3$;
$B^5$=H, F, Cl, $CH_3$, $CF_3$.

The compounds of the formula (I) and pharmaceutically acceptable solvates, N-oxides and salts thereof are hereinafter together referred to as "compound(s) according to this invention".

This invention is directed, in part, to a compound of the formula (I) and pharmaceutically acceptable solvates, N-oxides and salts thereof, for use as a medicament, preferably a medicament for animals, e.g. for treating parasitic infections such as helminth infections in animals. This invention also is directed, in part, to using at least one compound of the formula (I) and pharmaceutically acceptable solvates, N-oxides and salts thereof to prepare a medicament for treating an infection including diseases caused by such infections (e.g., parasitoses caused by a helminth infection) in animals.

This invention also is directed, in part, to novel spiroindoline compounds, methods for making the compounds, and intermediates thereof. The preferred embodiments specified in this description for the compounds represent likewise preferred embodiments for the intermediates.

This invention also is directed, in part, to pharmaceutical compositions. The pharmaceutical compositions comprise a) at least one spiroindoline compound according to this invention, preferably a novel spiroindoline compound, and b) at least one excipient, and/or at least one active compound (preferably anthelmintic compound) which differs in structure from the component a).

This invention also is directed, in part, to methods for treating a parasitic infection in animals, particularly a treatment of parasitoses caused by a helminth infection. The methods comprise administering at least one compound according to this invention to the animal.

This invention also is directed, in part, to a kit. The kit comprises at least one spiroindoline compound according to this invention, preferably a novel spiroindoline compound. In addition, the kit comprises at least one other component, such as another ingredient (e.g., an excipient or active ingredient), and/or an apparatus for combining the compound with another ingredient, and/or an apparatus for administering the compound, and/or a diagnostic tool.

Further benefits of Applicants' invention will be apparent to one skilled in the art from reading this specification.

DETAILED DESCRIPTION OF PREFERRED EMBODIMENTS

Compounds According to this Invention

The invention relates to compounds of formula (I) and pharmaceutically acceptable solvates, N-oxides and salts thereof for use as a medicament. The compounds generally correspond in structure to formula (I)

wherein
Y=O, S;
Q=—$CH_2$—$CH(CH_3)$—, —$CH_2$—$CH_2$—O—, —$CH_2$—$CH_2$—$CH_2$—O—, —$CH_2$—$CH_2$—$CH_2$—$CH_2$—O—, —$CH_2$—CH=CH—, —$CH_2$—$CH_2$—$CH_2$—;
$R^1$=H, F, Cl, $CH_3$, $OCH_3$, $CF_3$;
$R^2$=H, F, Cl, $CH_3$, $OCH_3$, $CF_3$;
$A^1$=H, halogen, $C_1$-$C_4$-alkyl;
$A^2$=H, halogen, $C_1$-$C_4$-alkyl, $C_1$-$C_4$-alkoxy, $C_1$-$C_4$-alkylthio, wherein $C_1$-$C_4$-alkyl, $C_1$-$C_4$-alkoxy and $C_1$-$C_4$-alkylthio are optionally perfluorinated such as $CF_3$, $OCF_3$, $SCF_3$;
$A^3$=H, halogen, $C_1$-$C_4$-alkyl;
$A^4$=H, halogen, $C_1$-$C_4$-alkyl;
B=H, F, Cl, $CH_3$, $CF_3$;
$B^2$=H, F, Cl, $CH_3$, $CF_3$, $NO_2$;
$B^3$=H, F, Cl, $CH_3$, $CF_3$, CN, $OCH_3$, $OCF_3$;
$B^4$=H, F, Cl, $CH_3$, $CF_3$;
$B^5$=H, F, Cl, $CH_3$, $CF_3$.

In a preferred compound of formula (I)
Y=O, S, preferably O;
Q=—$CH_2$—$CH(CH_3)$—, —$CH_2$—$CH_2$—$CH_2$—O—, —$CH_2$—$CH_2$—$CH_2$—$CH_2$—O—, —$CH_2$—CH=CH—, —$CH_2$—$CH_2$—$CH_2$—, preferably —$CH_2$—$CH_2$—$CH_2$—O—, —$CH_2$—$CH_2$—$CH_2$—$CH_2$—O—, —$CH_2$—CH=CH—, more preferably —$CH_2$—CH=CH—;
$R^1$=H, F, Cl, $CH_3$, $OCH_3$, $CF_3$;
$R^2$=H, F, Cl, $CH_3$, $OCH_3$, $CF_3$;
$A^1$=H, halogen, $C_1$-$C_4$-alkyl;
$A^2$=H, halogen, $C_1$-$C_4$-alkyl, $C_1$-$C_4$-alkoxy, $C_1$-$C_4$-alkylthio, wherein $C_1$-$C_4$-alkyl, $C_1$-$C_4$-alkoxy and $C_1$-$C_4$-alkylthio are optionally perfluorinated such as $CF_3$, $OCF_3$, $SCF_3$;
$A^3$=H, halogen, $C_1$-$C_4$-alkyl;
$A^4$=H, halogen, $C_1$-$C_1$-alkyl;
$B^1$=H, F, Cl, $CH_3$, $CF_3$;
$B^2$=H, F, Cl, $CH_3$, $CF_3$, $NO_2$;
$B^3$=H, F, Cl, $CH_3$, $CF_3$, CN, $OCH_3$, $OCF_3$;
$B^4$=H, F, Cl, $CH_3$, $CF_3$;
$B^5$=H, F, Cl, $CH_3$, $CF_3$.

In a more preferred compound of formula (I),
Y=O, S, preferably O;
Q=—$CH_2$—CH=CH—;
$R^1$=H, F, Cl, $CH_3$, $OCH_3$, $CF_3$;
$R^2$=H, F, Cl, $CH_3$, $OCH_3$, $CF_3$;
$A^1$=H, Cl;
$A^2$=H, F, Cl, Br, $CH_3$, $OCH_3$, $OCF_3$, $CF_3$, $SCF_3$;
$A^3$=H, Cl;
$A^4$=H, Cl;
$B^1$=H, F, Cl, $CH_3$, $CF_3$;
$B^2$=H, F, Cl, $CH_3$, $CF_3$;
$B^3$=H, F, Cl, $CH_3$, $CF_3$, CN, $OCH_3$, $OCF_3$;
$B^4$=H, F, Cl, $CH_3$, $CF_3$;
$B^5$=H, F, Cl, $CH_3$, $CF_3$.

In another preferred compound of formula (I),
Y=O, S;
Q=—$CH_2$—$CH(CH_3)$—, —$CH_2$—$CH_2$—O—, —$CH_2$—$CH_2$$CH_2$—O—, —$CH_2$—$CH_2$—$CH_2$—$CH_2$—O—, —$CH_2$—CH=CH—, —$CH_2$—$CH_2$—$CH_2$—;
$R^1$=H, F, Cl, $CH_3$, $OCH_3$, $CF_3$;
$R^2$=H, F, Cl, $CH_3$, $OCH_3$, $CF_3$;
$A^1$=H, halogen, $C_1$-$C_4$-alkyl;
$A^2$=H, halogen, $C_1$-$C_4$-alkyl, $OCF_3$, $SCF_3$, $CF_3$;
$A^3$=H, halogen, $C_1$-$C_4$-alkyl;
$A^4$=H, halogen, $C_1$-$C_4$-alkyl;
$B^1$=H, F, Cl, $CH_3$, $CF_3$;
$B^2$=H, F, Cl, $CH_3$, $CF_3$;

$B^3$=H, F, Cl, $CH_3$, $CF_3$, CN;
$B^4$=H, F, Cl, $CH_3$, $CF_3$;
$B^5$=H, F, Cl, $CH_3$, $CF_3$.

In another preferred compound of formula (I)
Y=O, S, preferably O;
Q=—$CH_2$—CH($CH_3$)—, —$CH_2$—$CH_2$—$CH_2$—O—, —$CH_2$—$CH_2$—$CH_2$—$CH_2$—O—, —$CH_2$—CH=CH—, —$CH_2$—$CH_2$—$CH_2$—, preferably —$CH_2$—$CH_2$—$CH_2$—O—, —$CH_2$—$CH_2$—$CH_2$—$CH_2$—O—, —$CH_2$—CH=CH—, more preferably —$CH_2$—CH=CH—;
$R^1$=H, F, Cl, $CH_3$, $OCH_3$, $CF_3$;
$R^2$=H, F, Cl, $CH_3$, $OCH_3$, $CF_3$;
$A^1$=H, halogen, $C_1$-$C_4$-alkyl;
$A^2$=H, halogen, $C_1$-$C_4$-alkyl, $OCF_3$, $SCF_3$, $CF_3$;
$A^3$=H, halogen, $C_1$-$C_4$-alkyl;
$A^4$=H, halogen, $C_1$-$C_4$-alkyl;
$B^1$=H, F, Cl, $CH_3$, $CF_3$;
$B^2$=H, F, Cl, $CH_3$, $CF_3$;
$B^3$=H, F, Cl, $CH_3$, $CF_3$, CN;
$B^4$=H, F, Cl, $CH_3$, $CF_3$;
$B^5$=H, F, Cl, $CH_3$, $CF_3$.

In still another preferred compound of formula (I),
Y=O, S, preferably O;
Q=—$CH_2$—CH=CH—;
$R^1$=H, F, Cl, $CH_3$, $OCH_3$, $CF_3$;
$R^2$=H, F, Cl, $CH_3$, $OCH_3$, $CF_3$;
$A^1$=H, Cl;
$A^2$=H, F, Cl, Br, $OCF_3$, $CF_3$;
$A^3$=H, Cl;
$A^4$=H, Cl;
$B^1$=H, F, Cl, $CH_3$, $CF_3$;
$B^2$=H, F, Cl, $CH_3$, $CF_3$;
$B^3$=H, F, Cl, $CH_3$, $CF_3$, CN;
$B^4$=H, F, Cl, $CH_3$, $CF_3$;
$B^5$=H, F, Cl, $CH_3$, $CF_3$.

In some preferred compounds of formula (I) at least one of the radicals $R^1$, $R^2$, $A^1$, $A^2$, $A^3$, $A^4$, $B^1$, $B^2$, $B^3$, $B^4$, $B^5$ is different from hydrogen.

In other preferred compounds of formula (I) at least one of the radicals $R^1$, $R^2$, $A^1$, $A^2$, $A^3$, $A^4$ is different from hydrogen.

In other preferred compounds of formula (I) at least one of the radicals $R^1$, $R^2$, $B^1$, $B^2$, $B^3$, $B^4$, $B^5$ is different from hydrogen.

In other preferred compounds of formula (I) at least one of the radicals $A^1$, $A^2$, $A^3$, $A^4$, $B^1$, $B^2$, $B^3$, $B^4$, $B^5$ is different from hydrogen.

In other preferred compounds of formula (I) at least one of the radicals $R^1$, $R^2$ is different from hydrogen.

In other preferred compounds of formula (I) at least one of the radicals $A^1$, $A^2$, $A^3$, $A^4$ is different from hydrogen.

In other preferred compounds of formula (I) at least one of the radicals $B^1$, $B^2$, $B^3$, $B^4$, $B^5$ is different from hydrogen.

In other preferred compounds of formula (I) at least two of the radicals $R^1$, $R^2$, $A^1$, $A^2$, $A^3$, $A^4$, $B^1$, $B^2$, $B^3$, $B^4$, $B^5$ are different from hydrogen.

In other preferred compounds of formula (I) at least one of the radicals $R^1$, $R^2$, $A^1$, $A^2$, $A^3$, $A^4$, $B^1$, $B^2$, $B^3$, $B^4$, $B^5$ is F or Cl.

In some preferred compounds of formula (I) at least one of the radicals $R^1$, $R^2$, $A^1$, $A^2$, $A^3$, $A^4$, $B^1$, $B^2$, $B^3$, $B^4$, $B^5$ is different from hydrogen and Q is —$CH_2$—CH=CH—.

In other preferred compounds of formula (I) at least one of the radicals $R^1$, $R^2$, $A^1$, $A^2$, $A^3$, $A^4$ is different from hydrogen and Q is —$CH_2$—CH=CH—.

In other preferred compounds of formula (I) at least one of the radicals $R^1$, $R^2$, $B^1$, $B^2$, $B^3$, $B^4$, $B^5$ is different from hydrogen and Q is —$CH_2$—CH=CH—.

In other preferred compounds of formula (I) at least one of the radicals $A^1$, $A^2$, $A^3$, $A^4$, $B^1$, $B^2$, $B^3$, $B^4$, $B^5$ is different from hydrogen and Q is —$CH_2$—CH=CH—.

In other preferred compounds of formula (I) at least one of the radicals $R^1$, $R^2$ is different from hydrogen and Q is —$CH_2$—CH=CH—.

In other preferred compounds of formula (I) at least one of the radicals $A^1$, $A^2$, $A^3$, $A^4$ is different from hydrogen and Q is —$CH_2$—CH=CH—.

In other preferred compounds of formula (I) at least one of the radicals $B^1$, $B^2$, $B^3$, $B^4$, $B^5$ is different from hydrogen and Q is —$CH_2$—CH=CH—.

In other preferred compounds of formula (I) at least two of the radicals $R^1$, $R^2$, $A^1$, $A^2$, $A^3$, $A^4$, $B^1$, $B^2$, $B^3$, $B^4$, $B^5$ are different from hydrogen and Q is —$CH_2$—CH=CH—.

In other preferred compounds of formula (I) at least one of the radicals $R^1$, $R^2$, $A^1$, $A^2$, $A^3$, $A^4$, $B^1$, $B^2$, $B^3$, $B^4$, $B^5$ is F or Cl and Q is —$CH_2$—CH=CH—.

a) Salts, Solvates and N-Oxides

A salt of the compounds of the formula (I) may be advantageous due to one or more of the salt's physical properties, such as pharmaceutical stability in differing temperatures and humidities; crystalline properties; and/or a desirable solubility in water, oil, or other solvent. In some instances, a salt may be used as an aid in the isolation, purification, and/or resolution of the compound. Acid and base salts can typically be formed by, for example, mixing the compound with an acid or base, respectively, using various known methods in the art. To the extent a salt of the compound is intended to be administered in vivo (i.e. to an animal) for a therapeutic benefit, the salt is pharmaceutically acceptable.

Salts may also be of advantage in the synthesis of the compounds according to this invention. For instance intermediates of the formula 7, may advantagously be used in form of their salts in the preparation process of the compounds according to this invention.

In general, an acid addition salt can be prepared by reacting a free base compound with an approximately stoichiometric amount of an inorganic or organic acid. Examples of often suitable inorganic acids for making (pharmaceutically acceptable) salts include hydrochloric, hydrobromic, hydroiodic, nitric, carbonic, sulfuric, and phosphoric acid. Examples of often suitable organic acids for making (pharmaceutically acceptable) salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

A solvate of a compound of the formula (I) may be formed by aggregation of said compound of the formula (I) with solvent molecules such as water, alcohols, for example ethanol, aromatic solvents such as toluene, ethers, halogenated organic solvents such as dichloromethane, preferably in a definite proportion by weight.

An N-oxide of a compound of the formula (I) may be formed by oxidation of an N-atom in an amine or N-heterocycle such as pyridine by oxidation agents such as hydrogen peroxide, peracids or inorganic oxidation agents such as potassium peroxymonosulfate (oxone).

b) Isomers

The compounds according to this invention and their intermediates may exist in various isomeric forms. A reference to a compound according to this invention or an intermediate thereof always includes all possible isomeric forms of such compound.

In some embodiments, a compound according to this invention may have two or more isomers, such as optical isomers or conformational isomers. For example, compounds with Q=—$CH_2$—CH=CH— can have a cis or trans configuration. In some preferred embodiments, such compound has the trans configuration, in other embodiments, the compound has the cis configuration. In a preferred embodiment this compound has trans configuration. For instance the compounds 1 to 6 and 10 to 99 of Table I below can have cis (Z) or trans (E) configuration, preferred is their trans (E) configuration.

Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound (Q=—$CH_2$—CH($CH_3$)—). In some embodiments, the compound is a non-chiral compound.

Treatment Methods Using Compounds According to this Invention

The compounds of the formula (I) and pharmaceutically acceptable solvates, N-oxides and salts thereof may generally be used as a medicament for animals. In some embodiments of this invention, one or more, preferably one compound according to this invention is administered to treat infections such as parasitic infections (e.g. helminth infections) of an animal (or make a medicament to treat infections such as parasitic infections of an animal). In one embodiment one or more, preferably one compound according to this invention is administered to treat parasitoses of an animal (or make a medicament to treat parasitoses of an animal).

The term "(parasitic) infection" includes conditions associated with or caused by one or more (parasitic) pathogens; said conditions include clinical conditions (parasitoses) and sub-clinical conditions. The term "treatment of parasitic infection" thus includes both the treatment of parasitoses and the treatment of sub-clinical conditions. The treatment of a parasite infection generally implies the suppression of parasite (e.g. helminth) burdens in the animal below that level at which economic loss occurs.

Sub-clinical conditions are typically conditions not directly leading to clinical symptoms in the parasite infected animal but leading to economic losses. Such economic losses can be e.g. by depression of growth in young animals, lower feed efficiency, lower weight gain in meat producing animals, lower milk production in ruminants, lower egg production in laying hens, or lower wool-production in sheep.

The term "parasitoses" relates to clinically manifest pathologic conditions and diseases associated with or caused by an infection by one or more parasites, such as, for example parasitic gastroenteritis or anemia in ruminants e.g. sheep and goats or colic in horses.

In general, the prevention or treatment of parasitic infection including parasitoses is achieved by administering one or more, preferably one compound according to this invention to treat a parasitic infection such as a helminth infection.

Thus the invention provides a method of treating a (parasitic) infection such as a helminth infection, including parasitoses, which comprises administering to the animal an antiparasitically, preferably an anthelmintically, effective amount of one or more compounds according to this invention. Preferably nematode, cestode or trematode infections are treated, more preferably nematode infections.

"Treating (parasitic) infections" includes treating parasitoses and means to partially or completely inhibit the development of (parasitic) infections of an animal susceptible to (parasitic) infection, reduce or completely eliminate the symptoms of infections of an animal having infections, and/or partially or completely cure infections of an animal having infections. This can be achieved by alleviating or reducing pathogen numbers such as parasite numbers in an animal.

Preferably "treating (parasitic) infections" means that the parasite count is reduced, after a first administration, by an amount ranging from 5% to about 100%. The effect of the compounds according to this invention can be e.g. ovicidal, larvicidal, and/or adulticidal or a combination thereof. The effect can manifest itself directly, i.e. killing the parasites either immediately or after some time has elapsed, for example when molting occurs, or by destroying their eggs, or indirectly, e.g. reducing the number of eggs laid and/or the hatching rate. Alternatively the parasite is not killed but paralyzed and is then dislodged and excreted by the host animal.

The compounds according to this invention may affect the movement, growth and viability of parasitic helminths, especially nematodes and may cause hypercontraction of the body wall muscles leading to paralysis or spasmodic contractions of body parts.

In a preferred embodiment the compounds according to this invention are used to treat a helminth infection, such as an infection caused by one or more helminths selected from the group consisting of a) cestodes: e.g. *Anaplocephala* spp.; *Dipylidium* spp.; *Diphyllobothrium* spp.; *Echinococcus* spp.; *Moniezia* spp.; *Taenia* spp.; b) trematodes e.g. *Dicrocoelium* spp.; *Fasciola* spp.; *Paramphistomum* spp.; *Schistosoma* spp.; or c) nematodes, e.g.; *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp. *Necator* spp.; *Nematodirus* spp.; *Nippostrongylus* spp.; *Oesophagostomum* spp.; *Onchocerca* spp.; *Ostertagia* spp.; *Oxyuris* spp.; *Parascaris* spp.; *Stephanurus* Spp.; *Strongylus* spp.; *Syngamus* spp.; *Toxocara* spp.; *Strongyloides* spp.; *Teladorsagia* spp.; Toxascaris spp.; *Trichinella* spp.; *Trichuris* spp.; *Trichostrongylus* spp.; *Triodontophorous* spp.; *Uncinaria* spp., and/or *Wuchereria* spp.; preferably nematode infections are treated, such as infections by *Trichostrongylus axei, Trichostrongylus colubriformis, Haemonchus contortus, Ascaridia galli,* and/or *Oesophagostomum dentatum.*

It is contemplated that the compounds according to this invention may be used to treat animals, including humans and non-human animals, especially non-human mammals. Such non-human mammals include, for example, livestock mammals (e.g., swine, livestock ruminats like bovines, sheep, goats, etc.), laboratory mammals (e.g., mice, rats, jirds, etc.), companion mammals (e.g., dogs, cats, equines, etc.), and wild and zoo mammals (e.g., buffalo, deer, etc.). It is contemplated that the compounds according to this invention also are suitable to treat non-mammals, such as poultry (e.g., turkeys, chickens, ducks, etc.) and fish (e.g., salmon, trout, koi, etc.).

In some embodiments, one or more, preferably one compound according to this invention is used to treat an infection by a helminth, such as a nematode, cestode or trematode, preferably a nematode (such as *Haemonchus contortus*), that is resistant to one or more other anthelmintic agents. In some embodiments, the compound according to this invention is active against a helminth, such as a nematode, cestode or trematode, preferably a nematode such as *Haemonchus contortus*, that is resistant to one or more of the following anthelmintics: an avermectin (e.g., ivermectin, selamectin, doramectin, abamectin, and eprinomectin); a milbemycin (moxidectin and milbemycin oxime); a pro-benzimidazole (e.g., febantel, netobimin, and thiophanate); a benzimidazole derivative, such as a thiazole benzimidazole derivative (e.g., thiabendazole and cambendazole) or a carbamate benzimidazole derivative (e.g., fenbendazole, albendazole (oxide), mebendazole, oxfendazole, parbendazole, oxibendazole, flubendazole, and triclabendazole); an imidazothiazole (e.g., levamisole and tetramisole); a tetrahydropyrimidine (morantel and pyrantel), an organophosphate (e.g., trichlorphon, haloxon, dichlorvos, and naphthalophos); a salicylanilide (e.g., closantel, oxyclozanide, rafoxanide, and niclosamide); a nitrophenolic compound (e.g., nitroxynil and nitroscanate); benzenedisulfonamide (e.g., clorsulon); a pyrazinoisoquinoline (e.g., praziquantel and epsiprantel); a heterocyclic compound (e.g., piperazine, diethylcarbamazine, and phenothiazine); dichlorophen, an arsenical (e.g., thiacetarsamide, melorsamine, and arsenamide); cyclooctadepsipeptide (e.g., emodepside); and a paraherquamide.

In some such embodiments, for example, the compound according to this invention is active against a helminth (for example, *Haemonchus contortus*) resistant to an avermectin, such as ivermectin. In other embodiments, the compound according to this invention is alternatively or additionally active against a helminth (for example, *Haemonchus contortus*) resistant to a benzimidazole derivative, such as fenbendazole. In other embodiments, the compound according to this invention is alternatively or additionally active against a helminth (for example, *Haemonchus contortus*) resistant to levamisole. And, in other embodiments, the compound according to this invention is alternatively or additionally active against a helminth (for example, *Haemonchus contortus*) resistant to pyrantel.

The compounds according to this invention may be administered in various dosage forms. The term "dosage form" means that the compounds according to this invention are formulated into a product suitable for administering to the animal via the envisaged dosage route. Such dosage forms are sometimes referred to herein as formulations or pharmaceutical composition.

Dosage forms useful in the current invention can be liquid, semi-solid or solid dosage forms.

Liquid dosage forms of the compounds are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily, or both. An emulsion is a heterogeneous dispersion of one immiscible liquid in another; it relies on an emulsifying agent for stability. A dry powder (or granule) for reconstitution is reconstituted as a solution or as a suspension immediately prior to injection. The principal advantage of this dosage form is that it overcomes the problem of instability in solution or suspension.

One possible dosage route is the oral dosage route, wherein the compound according to this invention is administered via the mouth. Oral dosage forms suitable for oral administration comprise liquids (e.g. drench or drinking water formulations), semi-solids (e.g. pastes, gels), and, solids (e.g. tablets, capsules, powders, granules, chewable treats, premixes and medicated blocks).

A drench is a liquid oral formulation that is administered directly into the mouth/throat of an animal, especially a livestock animal, by means of a "drench gun" or syringe or another suitable device. When the composition is administered in the animal recipient's drinking water or as a drench, it may be convenient to use a solution or suspension formulation. This formulation can be, for example, a concentrated suspension that is mixed with water or a dry preparation that is mixed and suspended in the water.

Semi-solid oral formulations (pastes or gels) are generally administered via an applicator directly into the mouth of an animal or mixed with the feed.

Solid oral formulations are either administered directly to an animal (tablet, capsule) or mixed with the feed or via medicated feed blocks.

When the oral formulation is administered via a non-human animal's feed, it may, for example, be fed as a discrete feed or as a chewable treat. Alternatively (or additionally), it may, for example, be intimately dispersed in the animal recipient's regular feed, used as a top dressing, or in the form of solid pellets, paste or liquid that is added to the finished feed. When the oral formulation is administered as a feed additive, it may be convenient to prepare a "premix" in which the oral formulation is dispersed in a liquid or solid carrier. This "premix" is, in turn, dispersed in the animal's feed using, for example, a conventional mixer.

Several modified-release delivery systems have been developed, that take advantage of the unique anatomy of the ruminant forestomach, i.e. for intra-ruminal administration. An intraruminal bolus is a specific formulation for ruminants (cattle, sheep, goats, buffalos, camelids, deer etc). It is a veterinary delayed release delivery system which remains in the rumeno-reticular sac of a ruminant animal over an extended period of time and in which the therapeutically active substance has a predictable and delayed release pattern. Such intraruminal boluses are usually administered using a balling gun or another suitable device.

It is contemplated that the compounds according to this invention may alternatively be administered via non-oral dosage routes, such as topically (e.g., via a spot-on, pour-on or transdermal patch), or parenterally (e.g., subcutaneous injection, intravenous injection, intramuscular injection, etc.).

For instance the compounds according to this invention may be administered topically using a transdermal formulation (i.e. a formulation that passes through the skin). Alternatively the compounds according to this invention may be administered topically via the mucosa.

Topical dosage forms suitable for topical administration comprise liquids (e.g. bath, spray, spot-on), semi-solids (e.g. creams, gels), and solids (e.g. patches, powders, collars). Typical topical formulations for animals are liquid or semi-liquid dosage forms. Typical formulations for transdermal and mucosal administration include, for example, pour-ons, spot-ons, dips, sprays, mousses, shampoos, powders, gels, hydrogels, lotions, solutions, Pharmaceutical Compositions This invention also is directed to pharmaceutical compositions (or medicaments) comprising one or more, preferably one compound according to this invention. The compositions also may (and preferably will) comprise one or more pharmaceutically acceptable excipients.

Pharmaceutical compositions of the present invention may be manufactured by, for example, processes known in the art. These processes include, for example, a variety of known mixing, dissolving, granulating, emulsifying, encapsulating, entrapping, and lyophilizing processes. Optimal formulation depends on, for example, the dosage route (e.g. oral, injection, topical).

Solid dosage forms, for example, may be prepared by, for example, intimately and uniformly mixing the compounds with fillers, binders, lubricants, glidants, disintegrants, flavoring agents (e.g., sweeteners), buffers, preservatives, pharmaceutical-grade dyes or pigments, and controlled release agents.

Oral dosage forms other than solids may be prepared by mixing the compounds with, for example, one or more solvents, viscosity-enhan creams, ointments, dusting powders, dressings, foams, films, skin patches, limb bands, collars, ear tags, wafers, sponges, fibers, bandages, and microemulsions. When a liquid formulation is used topically on skin, it can be administered by, for example, pouring on (pour-on or spot-on), spreading, rubbing, atomizing, spraying, dipping, bathing, or washing.

The pour-on or spot-on methods, for example, comprise applying the formulation to a specific location of the skin or coat, such as on the neck or backbone of the animal. This may be achieved by, for example, applying a swab or drop of the pour-on or spot-on formulation to a relatively small area of the recipient animal's skin or coat (i.e., generally no greater than about 10% of the animal recipient's skin or coat). In some embodiments, the compound according to this invention is dispersed from the application site to wide areas of the fur due to the spreading nature of the components in the formulation and the animal's movements while, in parallel, being absorbed through the skin and distributed via the animal recipient's fluids and/or tissues.

Parenteral formulations and delivery systems for non-oral routes comprise liquids (e.g. solutions, suspensions, emulsions, and dry powders for reconstitution), semi-solids and solids (e.g. implants). The majority of implants that are used in veterinary medicine are compressed tablets or dispersed matrix systems in which the drug is uniformly dispersed within a nondegradable polymer or alternatively extrusion products.

cing agents, surfactants, preservatives, stabilizers, resins, fillers, binders, lubricants, glidants, disintegrants, co-solvents, sweeteners, flavorings, perfuming agents, buffers, suspending agents, and pharmaceutical-grade dyes or pigments.

Contemplated binders include, for example, gelatin, *acacia*, and carboxymethyl cellulose.

Contemplated lubricants include, for example, magnesium stearate, stearic acid, and talc.

Contemplated disintegrants include, for example, corn starch, alginic acid, sodium carboxymethylcellulose, and sodium croscannellose.

Contemplated buffers include, for example, sodium citrate, and magnesium and calcium carbonate and bicarbonate.

Contemplated solvents include, for example, water, petroleum, animal oils, vegetable oils, mineral oil, and synthetic oil. Physiological saline solution or glycols (e.g., ethylene glycol, propylene glycol, or polyethylene glycol) also may be included. The solvent preferably has sufficient chemical properties and quantity to keep the compounds solubilized at temperatures in which the composition is stored and used.

Contemplated viscosity-enhancing agents include, for example, polyethylene, methylcellulose, sodium carboxymethylcellulose, hydroxypropyl-methylcellulose, hydroxypropylcellulose, sodium alginate, carbomer, povidone, *acacia*, guar gum, xanthan gum, tragacanth, methylcellulose, carbomer, xanthan gum, guar gum, povidone, sodium carboxymethylcellulose, magnesium aluminum silicate, carboxyvinyl polymers, carrageenan, hydroxyethyl cellulose, laponite, water-soluble salts of cellulose ethers, natural gums, colloidal magnesium aluminum silicateor finely divided silica, homopolymers of acrylic acid crosslinked with an alkyl ether of pentaerythritol or an alkyl ether of sucrose, and carbomers.

Contemplated surfactants include, for example, polyoxyethylene sorbitan fatty acid esters; polyoxyethylene mono-alkyl ethers; sucrose monoesters; lanolin esters and ethers; alkyl sulfate salts; and sodium, potassium, and ammonium salts of fatty acids.

Contemplated preservatives include, for example, phenol, alkyl esters of parahydroxybenzoic acid (e.g., methyl p-hydroxybenzoate (or "methylparaben") and propyl p-hydroxybenzoate (or "propylparaben")), sorbic acid, o-phenylphenol benzoic acid and the salts thereof, chlorobutanol, benzyl alcohol, thimerosal, phenylmercuric acetate and nitrate, nitromersol, benzalkonium chloride, and cetylpyridinium chloride.

Contemplated stabilizers include, for example, chelating agents and antioxidants.

Solid dosage forms also may comprise, for example, one or more excipients to control the release of the compounds. For example, it is contemplated that the compounds may be dispersed in, for example, hydroxypropylmethyl cellulose. Some oral dosage forms (e.g., tablets and pills) also may be prepared with enteric coatings.

Topical dosage route uses, for example, a concentrated liquid or semi-liquid solution, suspension (aqueous or non-aqueous), emulsion (water-in-oil or oil-in-water), or micro-emulsion comprising a compounds dissolved, suspended, or emulgated in a pharmaceutically-acceptable liquid vehicle. In such embodiments, a crystallization inhibitor optionally may generally be present.

Such a pour-on or spot-on formulation can be prepared by dissolving, suspending, or emulsifying the compounds in a suitable skin-fitted solvent or solvent mixture. Other excipients may be included as well, such as, for example, a surfactant, colorant, antioxidant, stabilizer, adhesive, etc. Contemplated solvents include, for example, water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oil, DMF, liquid paraffin, silicone, dimethylacetamide, N-methylpyrrolidone, or 2,2-dimethyl-4-oxy-methylene-1,3-dioxolane.

In some embodiments, a topical formulation (particularly a pour-on or spot-on formulation) comprises a carrier that promotes the absorption or penetration of the compounds through the skin into the blood stream, other bodily fluids (lymph), and/or body tissue (fat tissue). Contemplated examples of dermal penetration enhancers include, for example, dimethylsulfoxide, isopropyl myristate, dipropylene glycol pelargonate, silicone oil, aliphatic esters, triglycerides, and fatty alcohols.

Topical formulations also (or alternatively) may comprise, for example, one or more spreading agents. These substances act as carriers that assist in distributing an active ingredient over the animal recipient's coat or skin. They may include, for example, isopropyl myristate, dipropylene glycol pelargonate, silicone oils, fatty acid esters, triglycerides, and/or fatty alcohols. Various spreading oil/solvent combinations also may be suitable, such as, for example, oily solutions, alcoholic and isopropanolic solutions (e.g., solutions of 2-octyl dodecanol or oleyl alcohol), solutions of esters of monocarboxylic acids (e.g., isopropyl myristate, isopropyl palmitate, lauric acid oxalic ester, oleic acid oleyl ester, oleic acid decyl ester, hexyl laurate, oleyl oleate, decyl oleate, and caproic acid esters of saturated fatty alcohols having a carbon chain of 12 to 18 carbons), solutions of esters of dicarboxylic acids (e.g., dibutyl phthalate, diisopropyl isophthalate, adipic acid diisopropyl ester, and di-n-butyl adipate), or solutions of esters of aliphatic acids (e.g., glycols). When the formulation comprises a spreading agent, it also may be advantageous to include a dispersant, such as, for example, pyrrolidin-2-one, N-alkylpyrrolidin-2-one, acetone, polyethylene glycol or ether or ester thereof, propylene glycol, or synthetic triglycerides.

When formulated in, for example, an ointment, it is contemplated that the compounds may be mixed with, for example, either a paraffinic or a water-miscible ointment base. When formulated in a cream, it is contemplated that the compounds may be formulated with, for example, an oil-in-water cream base. In some instances, the aqueous phase of the cream base includes, for example at least about 30% (w/w) of a polyhydric alcohol, such as propylene glycol, butane-1,3-diol, mannitol, sorbitol, glycerol, polyethylene glycol, or a mixture thereof.

Injectable formulations may be prepared according to, for example, the known art using suitable solvents, solubilizing agents, protecting agents, dispersing agents, wetting agents, and/or suspending agents. Contemplated carrier materials include, for example, water, ethanol, butanol, benzyl alcohol, glycerin, 1,3-butanediol, Ringer's solution, isotonic sodium chloride solution, bland fixed oils (e.g., synthetic mono- or diglycerides), vegetable oil (e.g., corn oil), dextrose, mannitol, fatty acids (e.g., oleic acid), dimethyl acetamide, surfactants (e.g., ionic and non-ionic detergents), N-methylpyrrolidone, propylene glycol, and/or polyethylene glycols (e.g., PEG 400). Contemplated solubilizing agents include, for example, polyvinyl pyrrolidone, polyoxyethylated castor oil, polyoxyethylated sorbitan ester, and the like. Contemplated protecting agents include, for example, benzyl alcohol, trichlorobutanol, p-hydroxybenzoic acid ester, n-butanol, and the like.

In some embodiments, a parenteral formulation is, for example, prepared from sterile powders or granules having one or more of the carriers materials discussed above for other formulations. The compounds is, for example, dissolved or suspended in a liquid comprising water, polyethylene glycol, propylene glycol, ethanol, corn oil, cottonseed oil, peanut oil, sesame oil, benzyl alcohol, sodium chloride, and/or various buffers. The pH generally may be adjusted, if necessary, with a suitable acid, base, or buffer.

Other inert ingredients may generally be added to the composition as desired. To illustrate, it is contemplated that these may include, for example, lactose, mannitol, sorbitol, calcium carbonate, sodium carbonate, tribasic calcium phosphate, dibasic calcium phosphate, sodium phosphate, kaolin, compressible sugar, starch, calcium sulfate, dextro or microcrystalline cellulose, colloidal silicon dioxide, starch, sodium starch glycolate, crospovidone, microcrystalline cellulose, tragacanth, hydroxypropylcellulose, pregelatinized starch, povidone, ethylcellulose, hydroxypropylcellulose, hydroxypropylmethylcellulose, and methylcellulose.

Further aspects regarding formulation of drugs and various excipients are found in, for example, Germaro, A. R., et al., eds., *Remington: The Science and Practice of Pharmacy* (Lippincott Williams & Wilkins, 20th Ed., 2000). Another source regarding formulation of drugs and various excipients is found in, for example, Liberman, H. A., et al., eds., *Pharmaceutical Dosage Forms* (Marcel Decker, New York, N.Y., 1980).

The concentration of the compounds according to this invention in the applied dosage form may vary widely depending on, for example, the dosage route. In general, the concentration is from about 1 to about 70% (by weight). In some such embodiments, for example, the concentration is from about 1 to about 50% (by weight), or from about 10 to about 50% (by weight). In other embodiments, the concentration is from about 35 to about 65% (by weight), from about 40 to about 60% (by weight), from about 45 to about 55% (by weight), or about 50% (by weight).

In another aspect the present invention thus provides a pharmaceutical composition comprising an anthelmintically effective amount of one or more, preferably one compound according to this invention and one or more pharmaceutically acceptable excipients.

The formulation type chosen for a dosage form in any instance will depend upon the particular purpose envisaged and the physical, chemical and biological properties of the compound according to this invention.

The compounds and pharmaceutical compositions according to this invention are useful in treating parasitic infections such as helminth infections of animals. An "effective amount," is the amount or quantity of a compound that is required to alleviate or reduce parasite numbers in an animal, and/or to inhibit the development of parasite infections in an animal, in whole or in part.

This amount is readily determined by observation or detection of the pathogen numbers such as parasite numbers both before and after contacting the sample of pathogens such as parasites including their stages with the compound according to this invention, directly and/or indirectly, e.g., by contacting articles, surfaces, foliage, or animals with the compound.

This can be evaluated by counting parasites (especially helminthes) directly after necroscopy of the host animal.

The reduction of parasite numbers, especially gastrointestinal helminth parasites can be alternatively measured in-directly by faecal egg or differential larval counts. In this case the effective amount of the compound is determined by the reduction of the number of excreted helminth eggs or larvae in the faeces of the treated animal before and after treatment. For an in vivo administration the compound according to this invention, is preferably administered to an animal in an effective amount which is synonymous with "pharmaceutically effective amount" or "anthelmintically effective amount".

A single administration of a compound according to this invention is typically sufficient to treat a parasitic infection such as a helminth infection, preferably a nematode, cestode or trematode infection, more preferably a nematode infection. Although such a single dose is typically preferred, it is contemplated that multiple doses can be used. When the compound according to this invention is orally administered, the total dose to treat a disease such as a helminth infection is generally greater than about 0.01 mg/kg (i.e., milligram of compound according to this invention per kilogram body weight of the treated animal). In some such embodiments, the total dose is from about 0.01 to about 100 mg/kg, from about 0.01 to about 50 mg/kg, from about 0.1 to about 25 mg/kg, or from about 1 to about 20. For sheep, for example, the dose is generally from about 0.5 to about 15 mg/kg, from about 1 to about 10 mg/kg. The same dose range may be suitable for other dosage routes. For example, in some embodiments, the same dose range is used for subcutaneous administration. The desired dose, however, may be less in some instances where the compound according to this invention is administered intravenously.

If the compound according to this invention is administered parenterally via an injection, the concentration of the compound according to this invention in the dosage form preferably is sufficient to provide the desired therapeutically effective amount of the compound according to this invention in a volume that is acceptable for parenteral administration.

Factors affecting the preferred dosage may include, for example, the parasite species infection to be treated and the development stages of the parasites, the type (e.g., species and breed), age, size, sex, diet, activity, and condition of the of the infected animal; the dosage route; pharmacological considerations, such as the activity, efficacy, pharmacokinetic, and toxicology profiles of the particular composition administered; and whether the compound according to this invention being administered as part of a combination of active ingredients. Thus, the preferred amount of the compound according to this invention can vary, and, therefore, can deviate from the typical dosages set forth above. Determining such dosage adjustments is generally within the skill of those in the art.

Examples of Contemplated Combination Therapies

The methods and pharmaceutical compositions of this invention encompass methods wherein a compound according to this invention is the sole active ingredient administered to the recipient animal. It is contemplated, however, that the methods and pharmaceutical compositions also encompass combination therapies wherein a compound is administered in combination with one or more other pharmaceutically acceptable active ingredients. The other active ingredient(s) may be, for example, one or more other compounds according to this invention. Alternatively (or additionally), the other active ingredient(s) may be one or more pharmaceutically acceptable compounds that are not compounds according to this invention. The other active ingredient(s) may target the same and/or different parasites and conditions.

Contemplated active ingredient(s) that may be administered in combination with the compounds include, for example, pharmaceutically acceptable anthelmintics, insecticides and acaricides, insect growth regulators, anti-inflammatories, anti-infectives, hormones, dermatological preparations (e.g., antiseptics and disinfectants), and immunobiologicals (e.g., vaccines and antisera) for disease prevention.

Therefore this invention is also directed to the use as a medicament of combinations comprising a) one or more compounds according to this invention with b) one or more pharmaceutically acceptable active compounds which differ in structure from component a). The active compounds b) are preferably anthelmintic compounds, more preferably selected from the group consisting of avermectins (e.g., ivermectin, selamectin, doramectin, abamectin, and eprinomectin); milbemycins (moxidectin and milbemycin oxime); pro-benzimidazoles (e.g., febantel, netobimin, and thiophanate); benzimidazole derivatives, such as a thiazole benzimidazole derivative (e.g., thiabendazole and cambendazole) or a carbamate benzimidazole derivatives (e.g., fenbendazole, albendazole (oxide), mebendazole, oxfendazole, parbendazole, oxibendazole, flubendazole, and triclabendazole); an imidazothiazoles (e.g., levamisole and tetramisole); a tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulfonamides (e.g., clorsulon); pyrazinoisoquinolines (e.g., praziquantel and epsiprantel); heterocyclic compounds (e.g., piperazine, diethylcarbamazine, and phenothiazine); dichlorophen, arsenicals (e.g., thiacetarsamide, melorsamine, and arsenamide); cyclooctadepsipeptides (e.g., emodepside); paraherquamides (e.g. derquantel); and amino-acetonitrile compounds (e.g. monepantel, AAD 1566); amidine compounds (e.g., amidantel and tribendimidin), including all pharmaceutically acceptable forms, such as salts, solvates or N-oxides.

Preferred combinations are comprising a) one compound selected from the group compounds 1 to 99 of Table I below (or salts, solvates or N-oxides, thereof) and b) one compound selected from the group consisting of anthelmintic avermectins (e.g., ivermectin, selamectin, doramectin, abamectin, emamectin and eprinomectin); milbemycins (moxidectin and milbemycin oxime); pro-benzimidazoles (e.g., febantel, netobimin, and thiophanate); benzimidazole derivatives, such as thiazole benzimidazole derivatives (e.g., thiabendazole and cambendazole), carbamate benzimidazole derivatives (e.g., fenbendazole, albendazole (oxide), mebendazole, oxfendazole, parbendazole, oxibendazole, flubendazole, and triclabendazole); imidazothiazoles (e.g., levamisole and tetramisole); tetrahydropyrimidines (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulfonamides (e.g., clorsulon); pyrazinoisoquinolines (e.g., praziquantel and epsiprantel); heterocyclic compounds (e.g., piperazine, diethylcarbamazine, and phenothiazine); dichlorophen, arsenicals (e.g., thiacetarsamide, melorsamine, and arsenamide); cyclooctadepsipeptides (e.g., emodepside); paraherquamides (e.g. derquantel); amino-acetonitrile compounds (e.g. monepantel, AAD 1566); tribendimidine (amidine compound); and amidantel (amidine compound); including all pharmaceutically acceptable forms, such as salts.

Preferred combinations comprise at least one compound selected from the group compounds 1 to 99 of Table I below (or salts, solvates or N-oxides, thereof) and abamectin, ivermectin, emamectin, eprinomectin, doramectin, moxidectin, milbemycin oxime; or.

closantel, oxyclozanide, rafoxanide, niclosamide; or nitroxynil, nitroscanate, clorsulon; or praziquantel and epsiprantel.

Examples of such combinations are combinations of one of the compounds 1 to 99 of Table I below with abamectin.

Other examples are combinations of one of the compounds 1 to 99 of Table I below with ivermectin.

Other examples are combinations of one of the compounds 1 to 99 of Table I below with emamectin.

Other examples are combinations of one of the compounds 1 to 99 of Table I below with eprinomectin.

Other examples are combinations of one of the compounds 1 to 99 of Table I below with doramectin.

Other examples are combinations of one of the compounds 1 to 99 of Table I below with moxidectin.

Other examples are combinations of one of the compounds 1 to 99 of Table I below with milbemycin oxime.

Other examples are combinations of one of the compounds 1 to 99 of Table I below with closantel.

Other examples are combinations of one of the compounds 1 to 99 of Table I below with oxyclozanide.

Other examples are combinations of one of the compounds 1 to 99 of Table I below with rafoxanide.

Other examples are combinations of one of the compounds 1 to 99 of Table I below with niclosamide.

Other examples are combinations of one of the compounds 1 to 99 of Table I below with nitroxynil.

Other examples are combinations of one of the compounds 1 to 99 of Table I below with nitroscanate.

Other examples are combinations of one of the compounds 1 to 99 of Table I below with clorsulon.

Other examples are combinations of one of the compounds 1 to 99 of Table I below with praziquantel.

Other examples are combinations of one of the compounds 1 to 99 of Table I below with epsiprantel.

Other examples are combinations of one of the compounds 1 to 99 of Table I below with emodepside; or Examples of such combinations are combinations of a salt of one of the compounds 1 to 99 of Table I below with abamectin.

Other examples are combinations of a salt of one of the compounds 1 to 99 of Table I below with ivermectin.

Other examples are combinations of a salt of one of the compounds 1 to 99 of Table I below with emamectin.

Other examples are combinations of a salt of one of the compounds 1 to 99 of Table I below with eprinomectin.

Other examples are combinations of a salt of one of the compounds 1 to 99 of Table I below with doramectin.

Other examples are combinations of a salt of one of the compounds 1 to 99 of Table I below with moxidectin.

Other examples are combinations of a salt of one of the compounds 1 to 99 of Table I below with milbemycin oxime.

Other examples are combinations of a salt of one of the compounds 1 to 99 of Table I below with closantel.

Other examples are combinations of a salt of one of the compounds 1 to 99 of Table I below with oxyclozanide.

Other examples are combinations of a salt of one of the compounds 1 to 99 of Table I below with rafoxanide.

Other examples are combinations of a salt of one of the compounds 1 to 99 of Table I below with niclosamide.

Other examples are combinations of a salt of one of the compounds 1 to 99 of Table I below with nitroxynil.

Other examples are combinations of a salt of one of the compounds 1 to 99 of Table I below with nitroscanate.

Other examples are combinations of a salt of one of the compounds 1 to 99 of Table I below with clorsulon.

Other examples are combinations of a salt of one of the compounds 1 to 99 of Table I below with praziquantel.

Other examples are combinations of a salt of one of the compounds 1 to 99 of Table I below with epsiprantel.

Other examples are combinations of a salt of one of the compounds 1 to 99 of Table I below with emodepside.

Examples of such combinations are combinations of a solvate of one of the compounds 1 to 99 of Table I below with abamectin.

Other examples are combinations of a solvate of one of the compounds 1 to 99 of Table I below with ivermectin.

Other examples are combinations of a solvate of one of the compounds 1 to 99 of Table I below with emamectin.

Other examples are combinations of a solvate of one of the compounds 1 to 99 of Table I below with eprinomectin.

Other examples are combinations of a solvate of one of the compounds 1 to 99 of Table I below with doramectin.

Other examples are combinations of a solvate of one of the compounds 1 to 99 of Table I below with moxidectin.

Other examples are combinations of a solvate of one of the compounds 1 to 99 of Table I below with milbemycin oxime.

Other examples are combinations of a solvate of one of the compounds 1 to 99 of Table I below with closantel.

Other examples are combinations of a solvate of one of the compounds 1 to 99 of Table I below with oxyclozanide.

Other examples are combinations of a solvate of one of the compounds 1 to 99 of Table I below with rafoxanide.

Other examples are combinations of a solvate of one of the compounds 1 to 99 of Table I below with niclosamide.

Other examples are combinations of a solvate of one of the compounds 1 to 99 of Table I below with nitroxynil.

Other examples are combinations of a solvate of one of the compounds 1 to 99 of Table I below with nitroscanate.

Other examples are combinations of a solvate of one of the compounds 1 to 99 of Table I below with clorsulon.

Other examples are combinations of a solvate of one of the compounds 1 to 99 of Table I below with praziquantel.

Other examples are combinations of a solvate of one of the compounds 1 to 99 of Table I below with epsiprantel.

Other examples are combinations of a solvate of one of the compounds 1 to 99 of Table I below with emodepside.

Examples of such combinations are combinations of an N-oxide of one of the compounds 1 to 99 of Table I below with abamectin.

Other examples are combinations of an N-oxide of one of the compounds 1 to 99 of Table I below with ivermectin.

Other examples are combinations of an N-oxide of one of the compounds 1 to 99 of Table I below with emamectin.

Other examples are combinations of an N-oxide of one of the compounds 1 to 99 of Table I below with eprinomectin.

Other examples are combinations of an N-oxide of one of the compounds 1 to 99 of Table I below with doramectin.

Other examples are combinations of an N-oxide of one of the compounds 1 to 99 of Table I below with moxidectin.

Other examples are combinations of an N-oxide of one of the compounds 1 to 99 of Table I below with milbemycin oxime.

Other examples are combinations of an N-oxide of one of the compounds 1 to 99 of Table I below with closantel.

Other examples are combinations of an N-oxide of one of the compounds 1 to 99 of Table I below with oxyclozanide.

Other examples are combinations of an N-oxide of one of the compounds 1 to 99 of Table I below with rafoxanide.

Other examples are combinations of an N-oxide of one of the compounds 1 to 99 of Table I below with niclosamide.

Other examples are combinations of an N-oxide of one of the compounds 1 to 99 of Table I below with nitroxynil.

Other examples are combinations of an N-oxide of one of the compounds 1 to 99 of Table I below with nitroscanate.

Other examples are combinations of an N-oxide of one of the compounds 1 to 99 of Table I below with clorsulon.

Other examples are combinations of an N-oxide of one of the compounds 1 to 99 of Table I below with praziquantel.

Other examples are combinations of an N-oxide of one of the compounds 1 to 99 of Table I below with epsiprantel.

Other examples are combinations of an N-oxide of one of the compounds 1 to 99 of Table I below with emodepside.

The compounds of the current invention can be combined with pharmaceutically acceptable insecticides or acaricides. Such pharmaceutically acceptable insecticides and acaricides include, for example, acetamiprid, acetoprole, amitraz, amidoflumet, avermectin, azadirachtin, bifenthrin, bifenazate, buprofezin, bistrifluron, chlorfenapyr, chlorfluazuron, chlorantraniliprole, chlorpyrifos, chromafenozide, clothianidin, cyantraniliprole, cyflumetofen, β-cyfluthrin, cyhalothrin, λ-cyhalothrin, cymiazole cypermethrin, cyromazine, deltamethrin, demiditraz, diafenthiuron, diazinon, diflubenzuron, dimefluthrin, dinotefuran, emamectin, esfenvalerate, ethiprole, fenoxycarb, fenpropathrin, fenvalerate, fipronil, flonicamid, flubendiamide, flucythrinate, tau-fluvalinate, flufenoxuron, halofenozide, hexaflumuron, imidacloprid, indoxacarb, lufenuron, metaflumizone, methoprene, metofluthrin, methoxyfenozide, nitenpyram, novaluron, noviflumuron, permethrin, phosmet, profluthrin, protrifenbute, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen, spirotetramat, sulfoxaflor, tebufenozide, tebufenpyrad, teflubenzuron, tefluthrin, tetrachlorvinphos, tetramethylfluthrin, thiacloprid, thiamethoxam, tolfenpyrad, tralomethrin, and triflumuron. General references discussing antiparasitic agents, such as insecticides and acaricides, include, for example, *The Pesticide Manual*, 13th Edition, C. D. S. Tomlin, Ed., British Crop Protection Council, Farnham, Surrey, U.K. (2003).

In some contemplated embodiments, the compounds are administered with pyridylmethylamine derivatives, such as, for example, pyridylmethylamine derivatives discussed in European Patent Appl. EP0539588 or Int'l Patent Appl. Publ. WO2007/115643.

In some contemplated embodiments, the compounds is administered with nodulisporic acids and derivatives thereof, such as, for example, compounds discussed in U.S. Pat. Nos. 5,399,582; 5,945,317; 5,962,499; 5,834,260; 6,221,894; or U.S. Pat. No. 5,595,991; or Int'l Patent Appl. Publ. 1996/29073.

Pharmaceutically acceptable insect growth regulators include, for example, methoprene, pyriproxyfen, tetrahydroazadirachtin, chlorfluazuron, cyromazine, diflubenzuron, fluazuron, flucycloxuron, flufenoxuron, hexaflumuron, lufenuron, ifenuron, tebufenozide, and triflumuron. These compounds tend to provide both initial and sustained treatment of parasite infections at all stages of insect development, including eggs, on the animal subject, as well as within the environment of the animal subject.

Other antiparasitic compounds contemplated to be useful in combination therapies with the compounds include, for example, imidazo[1,2-b]pyridazine compounds discussed in US Patent Appl. Publ. No. 2005-0182059; 1-(4-Mono and di-halomethylsulphonylphenyl)-2-acylamino-3-fluoropropanol compounds discussed U.S. Pat. No. 7,361,689; trifluoromethanesulfonanilide oxime ether compounds discussed in U.S. Pat. No. 7,312,248; n-[(phenyloxy)phenyl]-1,1,1-trifluoromethanesulfonamide and n-[(phenylsulfanyl)phenyl]-1,1,1-trifluoromethanesulfonamide compounds discussed in US Patent Appl. Publ. 2006-0281695; and 2-phenyl-3-(1H-pyrrol-2-yl)acrylonitrile compounds discussed in US Appl. Publ. 2006/0128779; isoxazoline compounds discussed in WO Patent Appl, Publ. 2005-085216, WO 2007-026965, WO 2007-070606, WO 2007-075459, WO 2007-079162, WO 2007-105814, WO 2007-125984, WO 2008-019760, WO 2008-122375, WO 2008-150393, WO 2009-002809, WO 2009-003075, WO 2009-022746, WO 2009-035004, WO 2009-045999, WO 2009-051956, WO 2009-035004.

In the contemplated combination therapies, the compounds according to this invention may be administered before, simultaneously, and/or after the other active ingredient(s). In addition, the compounds according to this invention may be administered in the same composition as the other active ingredient(s) and/or in separate compositions from the other active ingredient(s). Further, the compounds according to this invention and other active ingredient(s) may be administered via the same and/or different dosage route.

When the compounds according to this invention are administered in a combination therapy, the weight ratio of the active ingredients may vary widely. Factors influencing this ratio include, for example, the particular compounds; the identity of the other active ingredient(s) be administered in the combination therapy; the dosage route of the compounds and other active ingredient(s); the target condition and pathogen; the type (e.g., species and breed), age, size, sex, diet, activity, and condition of the animal; and pharmacological considerations, such as the activity, efficacy, pharmacokinetic, and toxicology profiles of the compounds and other active ingredient(s). In some contemplated embodiments, for example, the weight ratio of the compounds to the other active ingredient(s) is, for example, is from about 1:3000 to about 3000:1. In some such instances, the weight ratio is from about 1:300 to about 300:1. In other such instances, the weight ratio is from about 1:30 and about 30:1.

In addition to other active ingredients, it is contemplated that the compounds may be administered with one or more other compounds that beneficially affects (e.g. enhances or prolongs) the activity (or other characteristic, such as safety) of the compounds. For example, it is contemplated that the compounds may be administered with one or more synergists, such as, for example, piperonyl butoxide (PBO) and triphenyl phosphate (TPP). Other synergists include, for example, N-(2-ethylhexyl)-8,9,10-trinorborn-5-ene-2,3-dicarboxamide (also known as "ENT 8184" or "MGK 264") and Verbutin (also known as "MB-599").

This invention also is directed to kits that are, for example, suitable for use in performing the methods of treatment described above. The kit comprises a therapeutically effective amount of one or more spiroindoline compounds of this invention, and an additional component. The additional component(s) may be, for example, one or more of the following: another ingredient (e.g., an excipient or active ingredient), an apparatus for combining the compound of this invention with another ingredient and/or for administering the compound of this invention, or a diagnostic tool.

The compounds used according to this invention show an excellent activity in treating parasite infections and in addition are acceptable for the animals treated.

EXAMPLES

The following examples are merely illustrative, and not limiting to the remainder of the disclosure in any way.

The methods described in the examples can be easily adapted by a person skilled in the art to make other compounds according to this invention, and intermediates thereof. For instance, a person skilled in the art could replace in the examples the exemplified starting compounds by other compounds of the formulae 3, 5, 8 or 9 (e.g. commercially available compounds), perform routine adaptions of the reaction conditions, if any, and use them for the synthesis of further compounds according to this invention.

A: Synthesis of Compounds According to this Invention

The preparation of spiroindoline-3,4'-piperidine building blocks 4 is described in Scheme 1. A mixture of an appropriately substituted phenyl hydrazine 3 or corresponding hydrochloride and N-protected piperidine-4-carbaldehyde 1 or 4-(alkoxymethylene)piperidine 2 in the presence of an acid affords the formation of the intermediate indole (not shown). Suitable protecting groups (PG) for the nitrogen of 1 and 2 include, but are not limited to, preferably tert-butyl carbamate (Boc), benzyl carbamate (Cbz), allyl carbamate (Alloc), 9-fluorenylmethyl carbamate (Fmoc), and the like. Suitable acids include, but are not limited to, trifluoroacetic acid, p-toluenesulfonic acid and the like. Reduction of the intermediate indole to the indoline can be accomplished by a number of reducing agents. Suitable reducing agents include, but are not limited to, alkali metal aluminum hydrides such as lithium aluminium hydride, alkali metal borohydrides such as sodium borohydride and the like. The solvents include ethereal solvents such as tetrahydrofuran or dioxane, aromatic solvents such as toluene, alcoholic solvents such as ethanol, methanol, or isopropanol or mixtures thereof. The reaction temperature ranges from about −78° C. to 120° C., preferably about −20° C. to 80° C. A general procedure to 4 is described in Maligres, P. E; et al. *Tetrahedron* 1997, 53, 10983-10992. Other synthetic routes to spiroindoline-3,4'-piperidines 4 beside the Fischer indole type route, are disclosed in patent applications WO 2003-106457, WO 2006-090261, WO 2005-063745, WO 2008-157741.

Scheme 1

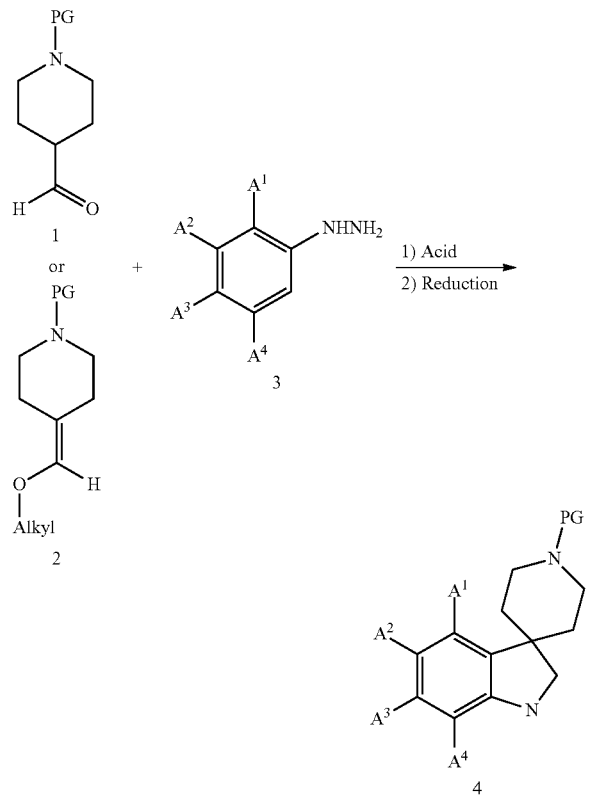

The spiroindoline-3,4'-piperidine isonicotinic acid amides 6 can be prepared by reacting spiroindole-3,4'-piperidines 4 with isonicotinic acyl halides 5 such as acyl chloride, as shown in Scheme 2. The acyl halides are readily formed using halogenation agents such as thionyl chloride, oxalyl chloride, thionyl bromide, cyanuric fluoride or N,N-diethylaminosulfur trifluoride. Pyridine-4-carbonyl halides 5 are coupled with amines 4 in the presence of a base in an inert solvent to afford the amides 6. Inorganic bases such as alkali metal carbonates, alkali metal hydrogencarbonates or alkali hydroxides can be used for the coupling as well as organic bases such as preferably tertiary amines such as trietylamine, diisopropylethylamine, etc., or aromatic amines such as pyridine or imidazole, etc. Also polymer bound bases such as polymer-supported 2-tert-butylimino-2-diethylamino-1, 3-dimethylperhydro-1,3,2-diazaphosphorine (BEMP) can be used for the amide coupling. Solvents utilized include lower halocarbon solvents such as dichloromethane, chloroform, etc., etheral solvents such as tetrahydrofuran, dioxane, etc. or amide solvents such as dimethylformamide, N-methylpyrrolidinone etc.

Scheme 2

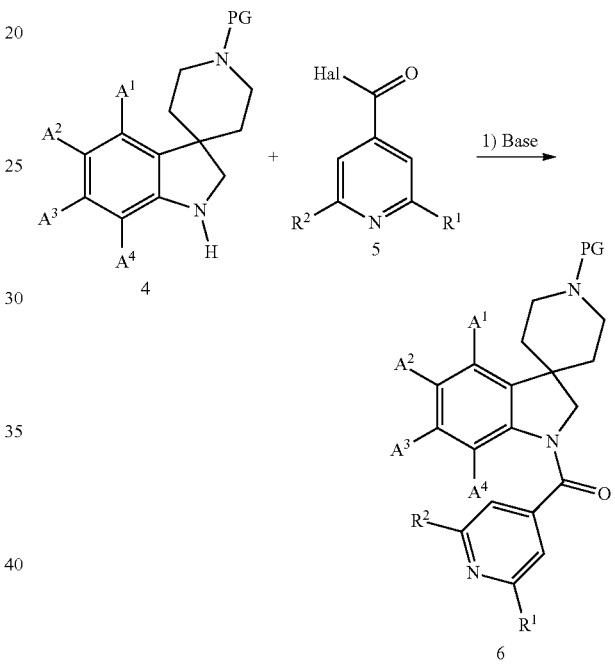

Numerous alternative methods are known to generate amides directly from carboxylic acids and amines utilizing coupling reagents such as carbodiimides (e.g. dicyclohexylcarbodiimide, 1-ethyl-3-(3-dimethylaminopropyl) carbodiimide hydrochloride), uronium/guanidinium salts such as N-[(1H-benzotriazol-1-yl)dimethylamino)methylene]-N-methyl-methanaminium hexafluorophosphate N-oxide (HBTU) or 1,1'-carbonyldiimidazole beside others. Active esters or mixed anhydrides of isonicotinic acids can also be used for the synthesis of amides 6. Other suitable amide coupling procedures are disclosed in Goodman, M.; Felix, A.; Moroder, L.; Toniolo, C. in volume E22a of *Methods of Organic Chemistry (Houben-Weyl), Synthesis of Peptides and Peptidomimetics*, 4th edition, Georg Thieme Verlag, Stuttgart—New York, 2002.

Amides 6 can be readily converted into corresponding thioamides utilizing Lawesson's Reagen or phosphorus pentasulfide in inert solvents like ethereal solvents such as tetrahydrofuran or dioxane or aromatic solvents such as toluene under reflux conditions. Thioamides can be further reacted in the same manner as the amides to afford corresponding thioamide analogs of 10.

The protected nitrogen of amide 6 can be deprotected by suitable deprotection procedures applicable for the particular protecting group to yield the spirocyclic amine 7. Suitable methods for deprotection are described by Greene and Wuts, in *Protective Groups in organic synthesis,* 3rd edition, John Wiley & Sons, Inc., New York, 1999. For example, if compound 6 is protected by tert-butyl-carbamate (Boc) suitable deprotection methods are, but are not limited to treatment with trifluoroacetic acid in dichloromethane or hydrochloric acid in anhydrous dioxane as shown in Scheme 3. The resulting piperidinium salts can be neutralized with base to yield the corresponding piperidines 7. Suitable bases include, but are not limited to alkali metal carbonates, alkali metal hydrogencarbonates, alkali hydroxides as well as organic bases such as tertiary amines etc.

—$CH_2$—$CH_2$—O—, —$CH_2$—$CH_2$—$CH_2$—O—, —CH=CH—, —$CH_2$—$CH_2$—, at a temperature between ambient temperature and 100° C. in an organic solvent such as tetrahydrofuran or ethanol or mixtures of solvents in the presence of an reducing agent such as borane-pyridine complex, sodium borohydride, sodium (triacetoxy)borohydride, sodium cyanoborohydride or such like, to produce a compound of formula 10.

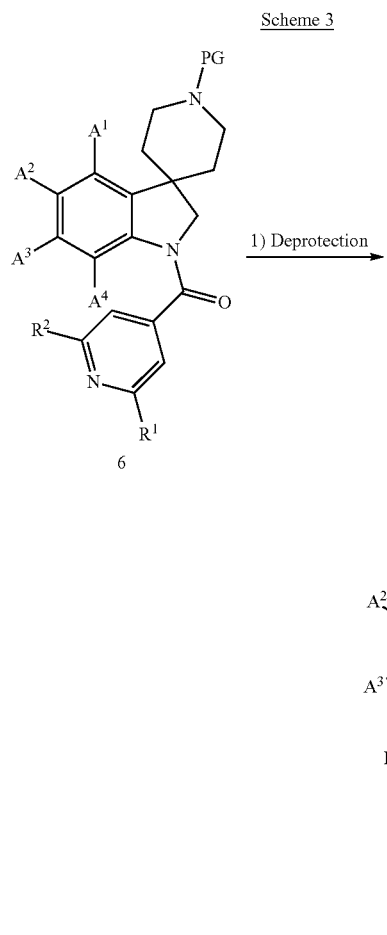

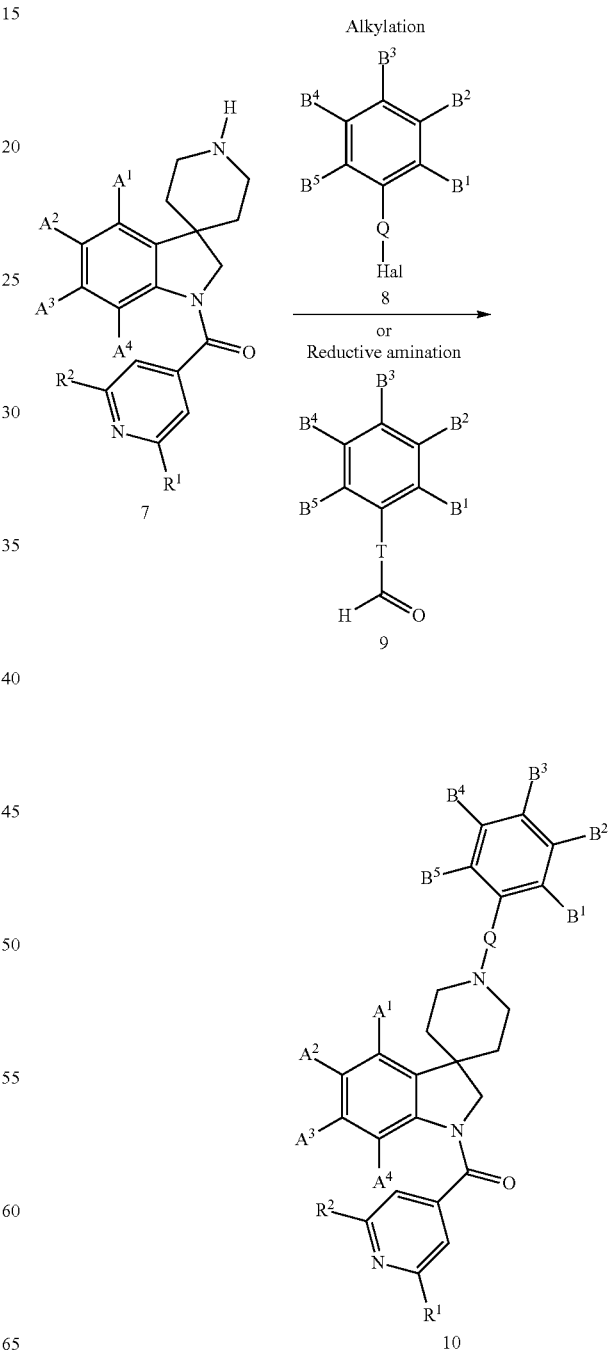

The spirocyclic amine 7 may be functionalized to a tertiary amine 10 by alkylation with an alkylation agent 8 or by reductive amination with suitable aldehydes 9 as shown in Scheme 4. Alkylation agents may be electrophiles containing halides such as iodo or preferably chloro and bromo and sulfonates such as p-toluenesulfonates, trifluoromethanesulfonates etc., which may be reacted in organic solvents such as dichloromethane, chloroform, 1,2-dichloroethane or preferably amide solvents such as dimethylformamide and N-methylpyrrolidinone, in the presence of suitable bases such as tertiary amines such as trietylamine, diisopropylethylamine, etc., or inorganic bases such as alkali metal carbonates, alkali metal hydrogencarbonates. Optionally, the alkylation may be catalyzed by halide salts such as sodium iodide, potassium iodide or tetrabutylammonium iodide. Alternatively, a compound of formula 7 may be reacted with an aldehyde 9, wherein T=—CH($CH_3$)—, —$CH_2$—O—, Alkylation agents 8 are preferably used for the preparation of 10. Suitable compounds are commercially available or can be prepared from corresponding carboxylic acids 11 or carboxylic acid esters 12 such as methyl ester or ethyl esters etc. (R³=methyl or ethyl) as shown in Scheme 5. Compounds 12 are reduced to alcohols then converted to halides preferably bromo and chloro, wherein T=—CH(CH₃)—, —CH₂—O—, —CH₂—CH₂—O—, —CH₂—CH₂—CH₂—O—, —CH=CH—, —CH₂—CH₂—. Suitable reducing agents include, but are not limited to, aluminum hydrides preferably lithium aluminum hydride, diisobutylaluminum hydride, borohydrides such as triethylborohydrides, borane dimethyl sulfide complex and triethoxysilane. Alcohols 13 can be converted to halides with various reagents; the most common are halogen acids and inorganic acid halides such as thionyl chloride, phosphorus pentachloride, phosphorus tribromide, phosphorus oxibromide. A favored halogenation procedure is the use of triphenylphosphine in combination with carbon tetrabromide or carbon tetrachloride in inert solvents such as dichloromethane. Several methods are known to a person skilled in the art to convert carboxylic acids to corresponding alcohols. A convenient procedure is for example the in situ transformation of 11 to the corresponding mixed anhydrides by reagents such as isobutyl chloroformate which can then be reduced to the corresponding alcohols 13 with several reducing agents such as sodium borohydride.

Example 1

2-chloro-4-pyridyl)-(5-chlorospiro[indoline-3,4'-piperidine]-1-yl)methanone (Intermediate of Formula 7

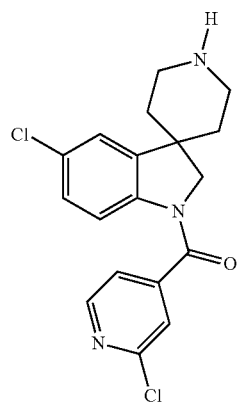 [SMILES: O=C(c1ccnc(Cl)c1)N1CC2(CCNCC2)c2cc(Cl)ccc21]

Step A: Tert-butyl-4-(methoxymethylene)piperidine-1-carboxylate

Methoxymethyl(triphenyl)phosphonium chloride (342.0 g, 1 mol) was suspended in ether (1100 ml). Within 30 min a solution of n-butyllithium in hexane (400 ml, 3.5 M, 1.4 mol) was added dropwise at −10° C. The resulting mixture was stirred for 1 h at 0-5° C. and afterwards a solution of tert-butyl-4-oxopiperidine-1-carboxylate (199.3 g, 1 mol) in ether (1100 ml) was added slowly at −20° C. The suspension was allowed to warm up to room temperature and was stirred for additional 2 h. The formed precipitate was filtered off, and washed with ether (300 ml). The filtrate and the com-

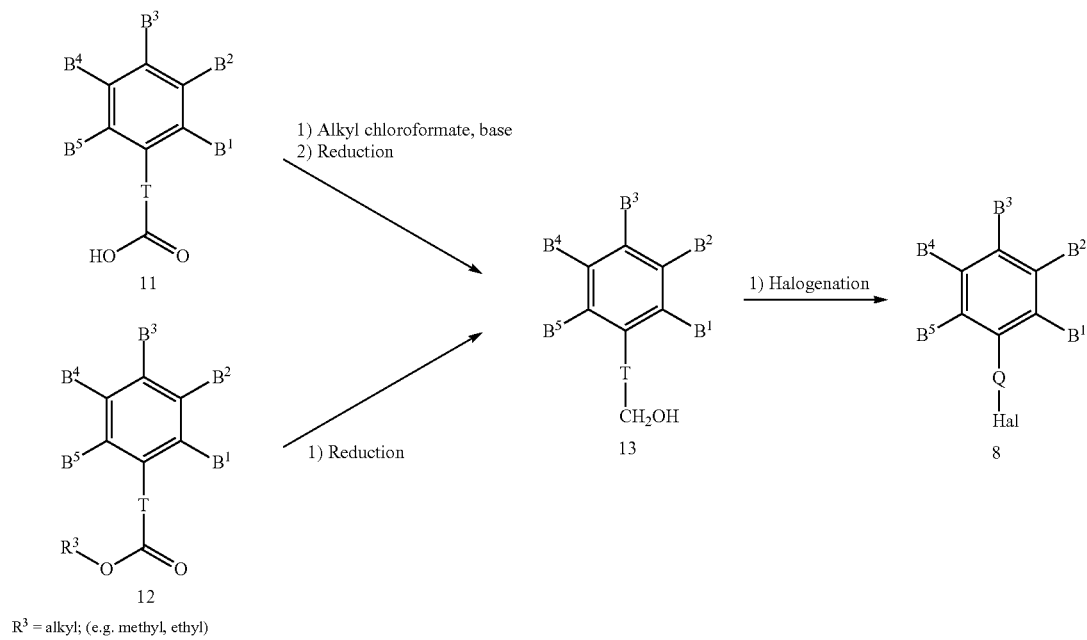

Scheme 5

Synthesis Examples

The following examples are for illustrative purposes only and are not intended to limit the scope of the invention. The compounds were named using Symyx® draw version 3.1.Net software (Symyx Technologies, Inc.)

bined organic washes were concentrated to give a yellow oil, which was then dissolved in tert-butyl methyl ether (270 ml) and washed with water (150 ml). The organic layer was separated and dried over magnesium sulfate. After removal of the organic solvent the crude product was purified by flash chromatography on a silica gel column (2.7 kg; 10 to 30% tert-butyl methyl ether/petrolether). 140 g (617 mmol, 62%) of the desired product as a light yellow oil were obtained. MS (ES) m/z=172.1 [M-tert-butyl+H]$^+$.

Step B: Tert-butyl 5-chlorospiro[indoline-3,4'-piperidine]-1'-carboxylate

Tert-butyl 4-(methoxymethylene)piperidine-1-carboxylate (6.0 g, 26.4 mmol) and 4-chlorophenylhydrazine hydrochloride (4.73 g, 26.4 mmol) were suspended in chloroform (300 ml) under an argon atmosphere. At 4° C. ethanol (0.5 ml) and trifluoroacetic acid (6.0 ml) were added sequentially to the stirred reaction mixture, which was allowed to stir overnight at 50° C. The dark green suspension was cooled down to room temperature and was poured into a mixture of ice water (250 ml) and concentrated ammonium hydroxide solution (100 ml) and was stirred for 90 min. The organic layer was separated and the aqueous phase was extracted with dichloromethane (3×50 ml). The combined organic phases were washed with brine, dried over anhydrous magnesium sulfate and concentrated to yield a brown solid which was further dried under vacuum. The crude tert-butyl 5-chlorospiro[indole-3,4'-piperidine]-1'-carboxylate was dissolved in ethanol (100 ml) and a suspension of sodium borohydride (3.1 g, 81.8 mmol) in ethanol (100 ml) was added within 30 min at room temperature while stirring. After 12 h the reaction mixture was concentrated and re-dissolved in dichloromethane. The organic phase was washed twice with water, afterwards with brine and dried over anhydrous magnesium sulfate. The organic solvent was removed to afford a brown solid (7.0 g, 21.7 mmol, 82%). The product was used for the next step without further purification.

MS (ES) m/z=323.1 [M+H]$^+$

Step C: 2-Chloropyridine-4-carbonyl chloride

2-Chloropyridine-4-carboxylic acid (20.0 g, 127 mmol) was added slowly to thionyl chloride (120 ml) at room temperature. After addition of dimethylformamide (0.05 ml) the reaction mixture was heated under reflux for 2.5 h. The thionyl chloride was removed in vacuo and the remaining liquid was diluted in toluene (100 ml). The solution was concentrated to afford a yellow oil (20.2 g, 115 mmol, 91%) which was taken to the next step without further purification.

Step D: Tert-butyl 5-chloro-1-(2-chloropyridine-4-carbonyl)spiro[indoline-3,4'-piperidine]-1'-carboxylate Tert-butyl 5-chlorospiro[indoline-3,4'-piperidine]-1'-carboxylate (30.0 g, 92.9 mmol) was dissolved in dichloromethane (200 ml) and triethylamine (11.3 g, 112 mmol) was added. A solution of 2-chloropyridine-4-carbonyl chloride (18.2 g, 103 mmol) in dichloromethane (50 ml) was added within 15 min at 0° C. The brown reaction mixture was allowed to warm up to room temperature and was stirred for 2 h. After addition of water (200 ml) the organic phase was separated, dried over anhydrous magnesium sulfate, followed by evaporation to afford a crude brown solid (36.1 g). The crude product was suspended in methanol (220 ml) and stirred at 0° C. After 2 h the solid was filtered off, washed with cold methanol and dried to yield a beige product (29.5 g, 63.8 mmol, 69%). The magnesium sulfate which was used to dry the dichloromethane phase was extracted with dichloromethane. After solvent evaporation another crop of a white crystalline product was obtained (9.1 g, 19.7 mmol, 21%). MS (ES) m/z=406 [M-tert-butyl+H]$^+$.

Step E: (2-chloro-4-pyridyl)-(5-chlorospiro[indoline-3,4'-piperidine]-1-yl)methanone Tert-butyl 5-chloro-1-(2-chloropyridine-4-carbonyl)spiro[indoline-3,4'-piperidine]-1'-carboxylate (38.0 g, 82.2 mmol) was slowly added to a vigorously stirred solution of HCl in dioxane (4 M, 500 ml) under nitrogen at room temperature. The reaction mixture was stirred at room temperature for 16 h. Then the suspension was poured on ice (750 g) and neutralized with 2000 ml of a sodium bicarbonate solution (10%) over a period of 2 h. The precipitate was filtered off and washed with water (500 ml) and ethyl acetate (200 ml). The remaining solid was dried at 50° C. in vacuo to afford a beige material (27 g, 74.5 mmol, 91%). MS (ES) m/z=363.1 [M+H]$^+$.

Example 2

[5-chloro-1'-[(E)-3-(2,3-dichlorophenyl)allyl]spiro[indoline-3,4'-piperidine]-1-yl]-(2-chloro-4-pyridyl)methanone (Compound 25)

Step A: (E)-3-(2,3-dichlorophenyl)prop-2-en-1-ol (E)-3-(2,3-dichlorophenyl)prop-2-enoic acid (1.09 g, 5.02 mmol) was dissolved in dry THF (25 ml). Triethylamine (607 mg, 6.0 mmol) was added and the solution was cooled to 0° C. Then, isobutyl chloroformate (785 mg, 5.75 mmol) was added and a white precipitate was formed immediately. The suspension was stirred for 1 h at 0° C. and the solids were filtered off. Water (1 ml) was added to the filtrate followed by the addition of sodium borohydride (378 mg, 10.0 mmol) in one portion. The solution was stirred for 1 h at 0° C. and then carefully quenched with 2N HCl solution. The solution was extracted with ethyl acetate and the organic layer was washed with saturated sodium chloride solution and finally dried over sodium sulfate. After concentration of the organic layer under reduced pressure, the crude product was purified by flash chromatography over a pre-packed silica column using a heptane/ethyl acetate gradient. After purification and concentration of the product fractions a white solid was obtained (998 mg, 4.91 mmol, 98% yield). MS (EI) m/z=204.1 M$^+$.

Step B: 1-[(E)-3-bromoprop-1-enyl]-2,3-dichloro-benzene (E)-3-(2,3-dichlorophenyl)prop-2-en-1-ol (998 mg, 4.91 mmol) was dissolved in dichloromethane (25 ml) and triphenylphosphine-polymer bound (3.2 g, 4.86 mmol, 1.52 mmol/g) was added. Tetrabromomethane (1.63 g, 4.91 mmol) was added and the suspension was stirred at ambient temperature for 1 h. The polymerbound triphenylphoshine was filtered off and the solvent was evaporated in vacuo. The crude mixture was purified by flash chromatography over a pre-packed silica column (100% heptane). After purification a colorless solid (1.01 g, 3.80 mmol, 77%) was obtained. MS (EI) m/z=266.0 M$^+$.

Step C: 2-Chloropyridine-4-carbonyl chloride

2-Chloropyridine-4-carboxylic acid (366 mg, 2.32 mmol) was suspended in dichloromethane (10 ml) and cooled to 0° C. Then, oxalyl chloride (1.47 g, 11.6 mmol) and a few drops of dimethylformamide were added to the suspension. The mixture was allowed to warm to ambient temperature and stirred for 1.5 h. The solvent and the excess of oxalyl chloride were removed in vacuo and co-evaporated with dry toluene (20 ml). The product was used without further purification in the next reaction.

Step D: Tert-butyl 5-chloro-1-(2-chloropyridine-4-carbonyl)spiro[indoline-3,4'-piperidine]-1'-carboxylate 2-Chloropyridine-4-carbonyl chloride (366 mg, 2.32 mmol) was dissolved in dichloromethane (10 ml) and a mixture of tert-butyl 5-chlorospiro[indoline-3,4'-piperidine]-1'-carboxylate (750 mg, 2.32 mmol, Example 1, step B) and triethylamine (705 mg, 6.97 mmol) in dichloromethane (5 ml) was added dropwise at 0° C. The ice water bath was removed and the mixture was stirred overnight at room temperature. A saturated aqueous solution of sodium carbonate was added and the organic layer was separated, dried over sodium sulfate and concentrated under reduced pressure. The crude mixture was purified by flash chromatography over a pre-packed silica column using a heptane/ethyl acetate gradient. The collected fractions gave an off-white solid (832 mg, 1.80 mmol, 78%) which is used without analysis in the next reaction.

Step E: (2-Chloro-4-pyridyl)-(5-chlorospiro[indoline-3,4'-piperidine]-1-yl)methanone Tert-butyl 5-chloro-1-(2-chloropyridine-4-carbonyl)spiro[indoline-3,4'-piperidine]-1'-carboxylate was stirred in a 1:1 mixture of dichloromethane/trifluoroacetic acid (20 ml) at room temperature for 1 h. Then the reaction mixture was quenched with a saturated aqueous solution of sodium bicarbonate. The layers were separated and the organic layer was dried over sodium sulfate. After evaporation in vacuo an off-white solid (650 mg, 1.79 mmol, 99%) was obtained. The product was used without further purification in the next reaction. MS (ES) m/z=362.0 [M+H]$^+$.

Step F: [5-Chloro-1'-[(E)-3-(2,3-dichlorophenyl)allyl]spiro[indoline-3,4'-piperidine]-1-yl]-(2-chloro-4-pyridyl)methanone (2-Chloro-4-pyridyl)-(5-chlorospiro[indoline-3,4'-piperidine]-1-yl)methanone (144 mg, 0.398 mmol) was dissolved in thy dimethylformamide (2 ml) and polymer-supported 2-tert-butylimino-2-diethylamino-1,3-dimethylperhydro-1,3,2-diazaphosphorine (BEMP) (399 mg, 0.878 mmol, 2.2 mmol/g) was added. The mixture was stirred at 60° C. for 30 min. 1-[(E)-3-bromoprop-1-enyl]-2,3-dichloro-benzene (158 mg, 0.594 mmol) and catalytic amounts of potassium iodide were added and the reaction mixture was stirred at 100° C. overnight. After cooling down to ambient temperature, the resin was filtered off and rinsed several times with dichloromethane. The filtrate was evaporated in vacuo. The crude mixture was purified by flash chromatography over a pre-packed silica column using a 99% heptane 1% triethylamine/ethyl acetate gradient. The remaining product was purified for a second time by flash chromatography over a pre-packed silica column using a gradient of 0.1 M ammonium hydroxide in dichloromethane and methanol. After the second purification step a white solid (118 mg, 0.216 mmol, 54% yield) was obtained. MS (ES) m/z=548.0 [M+H]$^+$

Example 3

Compounds 8, 14, 15, 26, 27, 30, 31, 33, 34, 35, 36, 49 and 50 were synthesized according to Example 2, using the appropriate starting compounds.

Example 4

2-Chloro-4-pyridyl)-[1'-[(E)-3-(3,4-difluorophenyl)allyl]-5-fluoro-spiro[indoline-3,4?-piperidine]-1-yl]methanone (Compound 55

Step A: Tert-butyl-5-fluorospiro[indole-3,4'-piperidine]-1'-carboxylate

Tert-butyl-4-(methoxymethylene)piperidine-1-carboxylate (7.0 g, 30.8 mmol) was suspended in tert-butyl methyl ether (50 ml) and acetonitrile (25 ml) and (4-fluorophenyl)hydrazine hydrochloride (5.0 g, 30.8 mmol) and ethanol (0.5 ml) were added. Within 10 min trifluoroacetic acid (9.1 g, 79.8 mmol) was added dropwise to the grey suspension at 20° C. The reaction mixture was stirred for 6 h at 50° C. and cooled down to room temperature. 25 ml of an ammonium hydroxide solution (25%) were added while stirring. The resulting red colored organic layer was washed with 15 ml brine and dried over sodium sulfate. After removal of organic solvents in vacuo a red oil (9.8 g) was obtained. The crude product was taken directly to the next step without further purification.

Step B: Tert-butyl-5-fluorospiro[indoline-3,4'-piperidine]-1'-carboxylate

Tert-butyl-5-fluorospiro[indole-3,4'-piperidine]-1'-carboxylate (9.8 g) was dissolved in 75 ml ethanol and cooled down to 10° C. Sodium borohydride (2.3 g, 62 mmol) was added slowly in four portions while keeping the temperature constant. The yellow reaction mixture was allowed to reach room temperature and was stirred for 20 h. The formed solid was filtered off and was washed with cold ethanol (20 ml). Then it was suspended in water (50 ml) and stirred for 30 min. The remaining solid material was filtered off, washed with water (25 ml) and dried in vacuo at 50° C. to afford a beige colored solid (3.6 g, 11.7 mmol, 38% over two steps) MS (ES) m/z=306.8 [M+H]$^+$.

Step C: Tert-butyl 1-(2-chloro-pyridine-4-carbonyl)-5-fluoro-spiro[indoline-3,4'-piperidine]-1'-carboxylate 2-Chloropyridine-4-carbonyl chloride (1.38 g, 7.84 mmol) was dissolved in dichloromethane (50 ml) under argon atmosphere and triethylamine (1.85 ml, 13.3 mmol) was added. A solution of tert-butyl-5-fluorospiro[indoline-3,4'-piperidine]-1'-carboxylate (1.50 g, 4.9 mmol) in 20 ml dichloromethane was added dropwise to the reaction mixture and stirred overnight at room temperature. The organic phase was washed 4 times with saturated sodium bicarbonate buffer, once with brine and was concentrated. The crude product was purified by flash chromatography over a silica gel column using an eluent consisting of dichloromethane and methanol 19:1. After concentration of the collected fractions the product was obtained as a red solid (1.6 g, 3.6 mmol, 73%). MS (ES) m/z=390.1 [M-tert-butyl+H]⁺.

Step D: (2-Chloro-4-pyridyl)-(5-fluorospiro[indoline-3,4'-piperidin-1-ium]-1-yl)methanone chloride Tert-butyl 1-(2-chloropyridine-4-carbonyl)-5-fluorospiro[indoline-3,4'-piperidine]-1'-carboxylate (5.46 g, 12.2 mmol) was slowly added to a vigorously stirred solution of HCl in dioxane (4 M, 35 ml) under nitrogen at room temperature. After 2 h the precipitate was filtered off, washed with dioxane and diethyl ether and dried in vacuo. The crude product (5 g) was used without further purification. MS (ES) m/z=345.9 [M+H]⁺.

Step E: (2-Chloro-4-pyridyl)-[1'-[(E)-3-(3,4-difluorophenyl)allyl]-5-fluoro-spiro[indoline-3,4'-piperidine]-1-yl]methanone (2-Chloro-4-pyridyl)-(5-fluorospiro[indoline-3,4'-piperidin-1-ium]-1-yl)methanone chloride (191 mg, 0.50 mmol) was dissolved in dry dimethylformamide and N,N-diisopropylethylamine (0.174 ml, 1 mmol) was added. A solution of 4-[(E)-3-bromoprop-1-enyl]-1,2-difluoro-benzene (117 mg, 0.50 mmol) in 0.5 ml dimethylformamide was added dropwise and stirred for 40 min at room temperature. The reaction mixture was quenched with water (5 ml) and dissolved with 20 ml dichloromethane. The organic phase was washed three times with water (20 ml), once with brine and dried over magnesium sulfate. The organic phase was concentrated and dried in vacuo. The remaining residue was dissolved in 3 ml acetonitrile and 0.1 ml dimethyl sulfoxide and purified by reversed phase chromatography using a Sunfire™ column (5 μm, 19×100 mm, Waters Corp.) and acetonitrile and aqueous 0.2% trifuoroacetic acid buffer as gradient. The combined product fractions were treated with saturated aqueous sodium bicarbonate buffer to obtain basic pH and the acetonitrile was evaporated. The remaining aqueous solution was extracted three times with dichloromethane. The combined organic phases were washed with brine and dried over magnesium sulfate. After removal of the solvent the beige product (56.7 mg, 0.114 mmol, 23%) was obtained. MS (ES) m/z=497.9 [M+H]⁺.

B: Analytics a) HPLC Methods

Method 1

HPLC-MS System:
  Agilent HPLC/MSD 1100 series composed of:
  Binary pump G 1312A included degasser G1379A, well plate sampler G1367A, column oven G1316A, diode array detector G1315B, mass detector G1946D SL with ESI-source and evaporating light detector Sedex 75.

Chromatographic System:
  Column: Atlantis dC18 from Waters, 4.6*50 mm, 3μ
  Oven: 30° C. ambient
  Injection: 2.0 μl
Eluents:
  Solvent A: water/formic acid: 99.9/0.1 vol./vol.
  Solvent B: acetonitrile/formic acid: 99.9/0.1 vol./vol.
  Flow: 1.0 ml/min Gradient:

| Time [min] | Solvent A [%] | Solvent B [%] |
|---|---|---|
| 0.0 | 95 | 5 |
| 1.0 | 95 | 5 |
| 5.0 | 2 | 98 |
| 7.0 | 2 | 98 |

Run time: 10 min (equilibration included)
Detection Methods:
  UV at 210 nm and 254 nm
  ESI/MS (100-1000 m/z), positive ions
  ELSD (Sedex 75)
Comment: Samples diluted in a 1 to 1 mixture of solvents A and B prior to analysis Method 2

HPLC-MS System:
  Agilent HPLC/MSD 1100 series composed of:
  Binary pump G 1312A included degasser G1379A, well plate sampler G1367A, column oven G1316A, diode array detector G1315B, mass detector G1946D SL with ESI-source and evaporating light detector Sedex 75.

Chromatographic System:
  Column: Chromolith Fast Gradient, RP-18e, 50*2 mm
  Oven: 35° C. ambient
  Injection: 1.0 μl
Eluents:
  Solvent A: water/formic acid=99.9/0.1 vol./vol.
  Solvent B: acetonitrile/formic acid=99.9/0.1 vol./vol.
  Flow: 1.2 ml/min Gradient:

| Time [min] | Solvent A [%] | Solvent B [%] |
|---|---|---|
| 0.0 | 90 | 10 |
| 2.0 | 0 | 100 |
| 2.7 | 0 | 100 |
| 3.0 | 90 | 10 |

Run time: 3.5 min (equilibration included)
Detection Methods:
UV at 254 nm, 210 nm
ESI/MS (100-1000 m/z), positive ions
ELSD (Sedex 75)
Comment: dilute samples in a mixture of solvent A and B 1:1 prior to analysis Method 3

HPLC-MS System:
  Agilent LC/MSD Trap 1100 series composed of:
  Binary pump G 1312A included degasser G1379A, well plate sampler G1367A, column oven G1316A, diode array detector G1315B, and mass detector G2445D with APCI-source.

Chromatographic System:
  Column: XBridge C18 von Waters, 4.6*50 mm, 2.5μ
  Oven: 40° C. ambient
  Injection: 2.0 μl
Eluents:
  Solvent A: water/ammonia: 99.9/0.1 vol./vol.
  Solvent B: acetonitrile 100%
  Flow: 1.0 ml/min Gradient:

| Time [min] | Solvent A [%] | Solvent B [%] |
|---|---|---|
| 0.0 | 90 | 10 |
| 4.0 | 0 | 100 |
| 5.0 | 0 | 100 |
| 5.5 | 90 | 10 |

Run time: 8 min (equilibration included)
Detection Methods:
UV at 254 nm, 210 nm
APCI/MS (100-1500 m/z), positive ions
Comment: Samples diluted in a 1 to 1 mixture of solvents A and B prior to analysis
Method 4
HPLC-MS System:
  Agilent LC/MSD 1100 SL series composed of:
  Diode array detector G1316A, mass detector Agilent LC/MSD-SL, evaporating light detector and Alltech ELSD2000,
Chromatographic System:
  Column: Phenomenex Gemini® C18, 150×4.6 mm, 5.0μ
  Oven: 35° C.
  Injection: 1.0 μl
Eluents:
  Solvent A: 10 mM formic acid in acetonitrile
  Solvent B: 10 mM formic acid in water
  Flow: 1 ml/min
Gradient:

| Time [min] | Solvent A [%] | Solvent B [%] |
|---|---|---|
| 0.0 | 2 | 98 |
| 10.5 | 98 | 2 |
| 18 | 98 | 2 |

Detection Methods:
UV at 320-220 nm
ESI/MS (100-800 m/z), positive and negative ions
ELSD (Alltech ELSD2000)
Comment: dilute samples in a mixture of solvent A and B 1:1 prior to analysis.
Method 5
HPLC-MS System:
  Agilent LC/MSD 1200 SL series composed of:
Diode array detector Agilent G1315D and mass detector Agilent LC/MSD-SL.
Chromatographic System:
  Column: Phenomenex Gemini® C18, 50×2.0 mm, 3μ.
  Oven: 30° C.
  Injection: 1 μl Eluents:
  Solvent A: water/formic acid: 99.9/0.1 vol./vol.
  Solvent B: acetonitrile/formic acid: 99.9/0.1 vol./vol.
  Flow: 0.8 ml/min Gradient:

| Time [min] | Solvent A [%] | Solvent B [%] |
|---|---|---|
| 0.0 | 98 | 2 |
| 3.5 | 2 | 98 |
| 6 | 2 | 98 |

Run Time:
Detection: UV 220 nm-320 nm; 270 nm
  ESI/MS (85-1000 m/z), positive ions
Comment: Samples diluted in a 1 to 1 mixture of solvents A and B prior to analysis
b) Analytical Data
  Table I below provides for each of 99 synthesized compounds of the formula (I) the structure, the calculated molecular weight (MW) (gram/mol), the observed MS signal (m/z), the HPLC retention time (RT) in minutes (min), and the HPLC-method used for analysis.
Compounds of Formula (I)

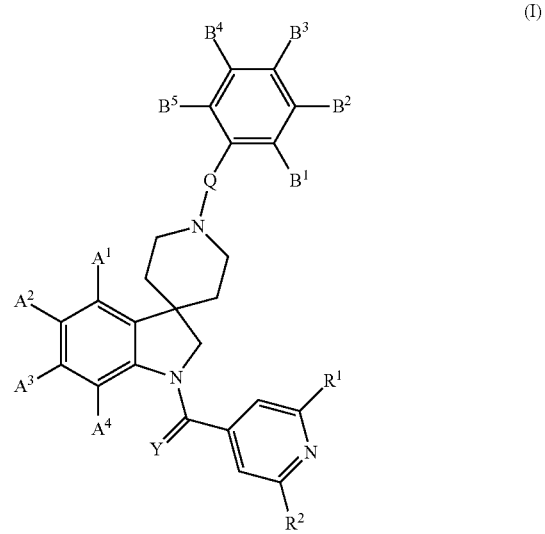

(I)

TABLE I

| No. | $A^1$ | $A^2$ | $A^3$ | $A^4$ | $B^1$ | $B^2$ | $B^3$ | $B^4$ | $B^5$ | $R^1$ | $R^2$ | Y | Q |
|---|---|---|---|---|---|---|---|---|---|---|---|---|---|
| 1 | H | Cl | H | H | H | H | F | H | H | H | Cl | O | (—$CH_2$—CH=CH—) (E) |
| 2 | H | Cl | H | H | H | H | $CF_3$ | H | H | H | Cl | O | (—$CH_2$—CH=CH—) (E,Z) |
| 3 | H | Cl | H | H | H | H | $CH_3$ | H | H | H | Cl | O | (—$CH_2$—CH=CH—) (E) |
| 4 | H | Cl | H | H | H | H | Cl | H | H | H | Cl | O | (—$CH_2$—CH=CH—) (E,Z) |
| 5 | H | Cl | H | H | H | H | F | H | F | H | Cl | O | (—$CH_2$—CH=CH—) (E) |
| 6 | H | Cl | H | H | H | H | H | H | H | $CH_3$ | Cl | O | (—$CH_2$—CH=CH—) (E) |
| 7 | H | Cl | H | H | H | H | $CH_3$ | H | H | H | Cl | O | (—$CH_2$—$CH_2$—O—) |
| 8 | H | Cl | H | H | H | H | F | H | H | H | Cl | O | (—$CH_2$—$CH_2$—$CH_2$—$CH_2$—O—) |
| 9 | H | Cl | H | H | H | H | F | H | H | H | Cl | O | (—$CH_2$—$CH_2$—$CH_2$—O—) |

TABLE I-continued

| | | | | | | | | | | | | | |
|---|---|---|---|---|---|---|---|---|---|---|---|---|---|
| 10 | H | Cl | H | H | H | H | H | H | H | Cl | Cl | O | (—CH$_2$—CH=CH—) (E) |
| 11 | H | Br | H | H | F | H | F | H | H | H | Cl | O | (—CH$_2$—CH=CH—) (E) |
| 12 | H | CF$_3$ | H | H | F | H | F | H | H | H | Cl | O | (—CH$_2$—CH=CH—) (E) |
| 13 | H | Cl | H | H | H | H | F | H | F | H | H | O | (—CH$_2$—CH=CH—) (E) |
| 14 | H | Cl | H | H | F | H | H | H | H | H | Cl | O | (—CH$_2$—CH=CH—) (E) |
| 15 | H | Cl | H | H | H | H | F | H | F | Cl | Cl | O | (—CH$_2$—CH=CH—) (E) |
| 16 | H | CF$_3$ | H | H | F | H | F | H | H | Cl | Cl | O | (—CH$_2$—CH=CH—) (E) |
| 17 | Cl | H | H | H | H | H | F | H | F | H | Cl | O | (—CH$_2$—CH=CH—) (E) |
| 18 | H | H | H | Cl | H | H | F | H | F | H | Cl | O | (—CH$_2$—CH=CH—) (E) |
| 19 | Cl | H | Cl | H | H | H | F | H | F | H | Cl | O | (—CH$_2$—CH=CH—) (E) |
| 20 | Cl | Cl | H | H | H | H | F | H | F | H | Cl | O | (—CH$_2$—CH=CH—) (E) |
| 21 | H | Cl | Cl | H | H | H | F | H | F | H | Cl | O | (—CH$_2$—CH=CH—) (E) |
| 22 | H | Cl | H | Cl | H | H | F | H | F | H | Cl | O | (—CH$_2$—CH=CH—) (E) |
| 23 | H | OCF$_3$ | H | H | H | H | F | H | F | H | Cl | O | (—CH$_2$—CH=CH—) (E) |
| 24 | H | Cl | H | H | H | H | H | H | Cl | H | Cl | O | (—CH$_2$—CH=CH—) (E) |
| 25 | H | Cl | H | H | H | H | H | Cl | Cl | H | Cl | O | (—CH$_2$—CH=CH—) (E) |
| 26 | H | Cl | H | H | H | H | Cl | H | Cl | H | Cl | O | (—CH$_2$—CH=CH—) (E) |
| 27 | H | Cl | H | H | H | H | Cl | Cl | H | H | Cl | O | (—CH$_2$—CH=CH—) (E) |
| 28 | H | F | H | H | H | H | F | H | F | Cl | O | | (—CH$_2$—CH=CH—) (E) |
| 29 | H | Cl | H | H | H | H | H | H | Cl | Cl | Cl | O | (—CH$_2$—CH=CH—) (E) |
| 30 | H | Cl | H | H | H | H | Cl | H | Cl | Cl | Cl | O | (—CH$_2$—CH=CH—) (E) |
| 31 | H | Cl | H | H | H | H | H | H | F | Cl | Cl | O | (—CH$_2$—CH=CH—) (E) |
| 32 | H | Cl | H | H | F | H | H | H | F | Cl | Cl | O | (—CH$_2$—CH=CH—) (E) |
| 33 | H | Cl | H | H | H | H | F | H | F | H | CH$_3$ | O | (—CH$_2$—CH=CH—) (E) |
| 34 | H | Cl | H | H | H | H | F | H | F | H | F | O | (—CH$_2$—CH=CH—) (E) |
| 35 | H | Cl | H | H | H | H | H | Cl | CH$_3$ | Cl | O | | (—CH$_2$—CH=CH—) (E) |
| 36 | H | Cl | H | H | H | H | Cl | H | Cl | CH$_3$ | Cl | O | (—CH$_2$—CH=CH—) (E) |
| 37 | H | Cl | H | H | H | H | H | H | F | CH$_3$ | Cl | O | (—CH$_2$—CH=CH—) (E) |
| 38 | H | Cl | H | H | F | H | H | H | F | CH$_3$ | Cl | O | (—CH$_2$—CH=CH—) (E) |
| 39 | H | Cl | H | H | H | H | F | H | F | H | CF$_3$ | O | (—CH$_2$—CH=CH—) (E) |
| 40 | H | Cl | H | H | F | F | F | F | F | Cl | Cl | O | (—CH$_2$—CH=CH—) (E) |
| 41 | H | Cl | H | H | H | H | F | F | H | H | Cl | O | (—CH$_2$—CH=CH—) (E) |
| 42 | H | CF$_3$ | H | H | H | H | Cl | H | H | H | Cl | O | (—CH$_2$—CH=CH—) (E) |
| 43 | H | F | H | H | H | H | F | H | F | H | CF$_3$ | O | (—CH$_2$—CH=CH—) (E) |
| 44 | H | OCF$_3$ | H | H | H | H | F | H | H | H | Cl | O | (—CH$_2$—CH=CH—) (E) |
| 45 | H | OCF$_3$ | H | H | H | H | F | F | H | H | Cl | O | (—CH$_2$—CH=CH—) (E) |
| 46 | H | Cl | H | H | H | H | F | H | H | CH$_3$ | CH$_3$ | O | (—CH$_2$—CH=CH—) (E) |
| 47 | H | Cl | H | H | H | H | CH$_3$ | H | H | CH$_3$ | CH$_3$ | O | (—CH$_2$—CH=CH—) (E) |
| 48 | H | Cl | H | H | H | H | F | H | F | CH$_3$ | CH$_3$ | O | (—CH$_2$—CH=CH—) (E) |
| 49 | H | CF$_3$ | H | H | H | H | F | H | H | H | Cl | O | (—CH$_2$—CH=CH—) (E) |
| 50 | H | CF$_3$ | H | H | H | H | CF$_3$ | H | H | H | Cl | O | (—CH$_2$—CH=CH—) (E) |
| 51 | H | Cl | H | H | H | H | Cl | H | F | H | Cl | O | (—CH$_2$—CH=CH—) (E) |
| 52 | H | Cl | H | H | F | H | H | H | Cl | H | Cl | O | (—CH$_2$—CH=CH—) (E) |
| 53 | H | Cl | H | H | F | H | H | F | Cl | Cl | O | | (—CH$_2$—CH=CH—) (E) |
| 54 | H | Cl | H | H | H | H | Cl | Cl | H | H | F | O | (—CH$_2$—CH=CH—) (E) |
| 55 | H | F | H | H | H | H | F | F | H | H | Cl | O | (—CH$_2$—CH=CH—) (E) |
| 56 | H | Cl | H | H | H | H | Cl | H | Cl | H | CH$_3$ | O | (—CH$_2$—CH=CH—) (E) |
| 57 | H | Cl | H | H | H | Cl | H | H | H | H | Cl | O | (—CH$_2$—CH=CH—) (E) |
| 58 | H | Cl | H | H | Cl | H | H | H | F | Cl | Cl | O | (—CH$_2$—CH=CH—) (E) |
| 59 | H | Cl | H | H | H | F | Cl | H | H | Cl | H | O | (—CH$_2$—CH=CH—) (E) |
| 60 | H | Cl | H | H | H | Cl | H | F | H | Cl | H | O | (—CH$_2$—CH=CH—) (E) |
| 61 | H | F | H | H | H | H | CH$_3$ | H | H | Cl | H | O | (—CH$_2$—CH=CH—) (E) |
| 62 | H | Cl | H | H | H | H | Cl | H | F | H | | O | (—CH$_2$—CH=CH—) (E) |
| 63 | H | Cl | H | H | H | H | CH$_3$ | H | H | CH$_3$ | Cl | O | (—CH$_2$—CH=CH—) (E) |
| 64 | H | Cl | H | H | F | F | F | F | F | CH$_3$ | Cl | O | (—CH$_2$—CH=CH—) (E) |
| 65 | H | OCF$_3$ | H | H | H | H | CH$_3$ | H | H | Cl | H | O | (—CH$_2$—CH=CH—) (E) |
| 66 | H | F | H | H | H | H | CN | H | H | Cl | H | O | (—CH$_2$—CH=CH—) (E) |
| 67 | H | F | H | H | Cl | H | Cl | H | H | Cl | H | O | (—CH$_2$—CH=CH—) (E) |
| 68 | H | CF$_3$ | H | H | Cl | H | Cl | H | H | Cl | H | O | (—CH$_2$—CH=CH—) (E) |
| 69 | H | F | H | H | F | H | F | H | H | Cl | H | O | (—CH$_2$—CH=CH—) (E) |
| 70 | H | F | H | H | F | H | H | H | H | Cl | Cl | O | (—CH$_2$—CH=CH—) (E) |
| 71 | H | CH$_3$ | H | H | H | Cl | Cl | H | H | Cl | H | O | (—CH$_2$—CH=CH—) (E) |
| 72 | H | Cl | H | H | H | F | CF$_3$ | H | H | Cl | H | O | (—CH$_2$—CH=CH—) (E) |
| 73 | H | Cl | H | H | CF$_3$ | H | F | H | H | Cl | H | O | (—CH$_2$—CH=CH—) (E) |
| 74 | H | Cl | H | H | F | H | CF$_3$ | H | H | Cl | H | O | (—CH$_2$—CH=CH—) (E) |
| 75 | H | Cl | H | H | H | NO$_2$ | H | H | H | Cl | H | O | (—CH$_2$—CH=CH—) (E) |
| 76 | H | Cl | H | H | H | H | H | H | H | Cl | H | S | (—CH$_2$—CH=CH—) (E) |
| 77 | H | SCF$_3$ | H | H | H | Cl | Cl | H | H | Cl | H | O | (—CH$_2$—CH=CH—) (E) |
| 78 | H | CH$_3$ | H | H | F | H | F | H | H | Cl | H | O | (—CH$_2$—CH=CH—) (E) |
| 79 | H | CH$_3$ | H | H | Cl | H | Cl | H | H | Cl | H | O | (—CH$_2$—CH=CH—) (E) |
| 80 | H | CH$_3$ | H | H | H | Cl | Cl | H | H | F | H | O | (—CH$_2$—CH=CH—) (E) |
| 81 | H | F | H | H | H | F | H | H | H | Cl | H | O | (—CH$_2$—CH=CH—) (E) |
| 82 | H | CF$_3$ | H | H | F | H | F | H | F | Cl | H | O | (—CH$_2$—CH=CH—) (E) |
| 83 | H | F | H | H | F | H | H | F | H | Cl | H | O | (—CH$_2$—CH=CH—) (E) |
| 84 | H | F | H | H | H | H | H | F | H | Cl | H | O | (—CH$_2$—CH=CH—) (E) |
| 85 | H | CH$_3$ | H | H | H | H | Cl | H | H | Cl | H | O | (—CH$_2$—CH=CH—) (E) |
| 86 | H | CH$_3$ | H | H | H | H | F | H | H | Cl | H | O | (—CH$_2$—CH=CH—) (E) |
| 87 | H | CH$_3$ | H | H | F | H | Cl | H | H | Cl | H | O | (—CH$_2$—CH=CH—) (E) |
| 88 | H | CH$_3$ | H | H | H | H | OCF$_3$ | H | H | Cl | H | O | (—CH$_2$—CH=CH—) (E) |
| 89 | H | OCH$_3$ | H | H | H | Cl | Cl | H | H | Cl | H | O | (—CH$_2$—CH=CH—) (E) |

TABLE I-continued

| | | | | | | | | | | | | | |
|---|---|---|---|---|---|---|---|---|---|---|---|---|---|
| 90 | H | OCH₃ | H | H | H | H | CF₃ | H | H | Cl | H | O | (—CH₂—CH=CH—) (E) |
| 91 | H | OCH₃ | H | H | H | H | Cl | H | H | Cl | H | O | (—CH₂—CH=CH—) (E) |
| 92 | H | OCH₃ | H | H | H | H | F | H | H | Cl | H | O | (—CH₂—CH=CH—) (E) |
| 93 | H | OCH₃ | H | H | F | H | F | H | H | Cl | H | O | (—CH₂—CH=CH—) (E) |
| 94 | H | OCH₃ | H | H | F | H | Cl | H | H | Cl | H | O | (—CH₂—CH=CH—) (E) |
| 95 | H | CH₃ | H | H | H | H | CH₃ | H | H | Cl | H | O | (—CH₂—CH=CH—) (E) |
| 96 | H | CH₃ | H | H | H | H | OCH₃ | H | H | Cl | H | O | (—CH₂—CH=CH—) (E) |
| 97 | H | CH₃ | H | H | H | H | CF₃ | H | H | Cl | H | O | (—CH₂—CH=CH—) (E) |
| 98 | H | CH₃ | H | H | F | H | H | H | H | Cl | H | O | (—CH₂—CH=CH—) (E) |
| 99 | H | OCH₃ | H | H | H | H | CH₃ | H | H | Cl | H | O | (—CH₂—CH=CH—) (E) |

| No. | MW calculated (g/mol) | m/z | RT (min) | HPLC Method |
|---|---|---|---|---|
| 1 | 496.41 | 496 | 1.465 | METHOD 2 |
| 2 | 546.42 | 546 | 4.787, 4.834 (E,Z) | METHOD 1 |
| 3 | 492.45 | 492 | 1.513 | METHOD 2 |
| 4 | 512.87 | 512 | 4.742, 4.785 (E,Z) | METHOD 1 |
| 5 | 514.40 | 514 | 4.649 | METHOD 1 |
| 6 | 492.45 | 492 | 1.543 | METHOD 2 |
| 7 | 496.44 | 496 | 4.685 | METHOD 1 |
| 8 | 528.45 | 528 | 2.789 | METHOD 5 |
| 9 | 514.43 | 514 | 4.509 | METHOD 1 |
| 10 | 512.87 | 512 | 4.887 | METHOD 1 |
| 11 | 558.85 | 560 | 4.481 | METHOD 1 |
| 12 | 547.95 | 548 | 4.513 | METHOD 1 |
| 13 | 479.96 | 480 | 4.430 | METHOD 1 |
| 14 | 496.41 | 496 | 2.740 | METHOD 5 |
| 15 | 548.85 | 548 | 2.966 | METHOD 5 |
| 16 | 582.40 | 582 | 1.624 | METHOD 2 |
| 17 | 514.40 | 514 | 1.557 | METHOD 2 |
| 18 | 514.40 | 514 | 1.486 | METHOD 2 |
| 19 | 548.85 | 548 | 1.616 | METHOD 2 |
| 20 | 548.85 | 548 | 1.654 | METHOD 2 |
| 21 | 548.85 | 550 | 1.634 | METHOD 2 |
| 22 | 548.85 | 548 | 1.506 | METHOD 2 |
| 23 | 563.95 | 564 | 1.645 | METHOD 2 |
| 24 | 512.87 | 514 | 1.535 | METHOD 2 |
| 25 | 547.31 | 548 | 3.006 | METHOD 5 |
| 26 | 547.31 | 548 | 2.993 | METHOD 5 |
| 27 | 547.31 | 548 | 3.216 | METHOD 4 |
| 28 | 532.39 | 532 | 1.651 | METHOD 2 |
| 29 | 547.31 | 548 | 1.645 | METHOD 2 |
| 30 | 581.76 | 582 | 3.021 | METHOD 5 |
| 31 | 530.86 | 530 | 2.905 | METHOD 5 |
| 32 | 548.85 | 548 | 1.619 | METHOD 2 |
| 33 | 493.98 | 494 | 2.636 | METHOD 5 |
| 34 | 497.95 | 498 | 2.836 | METHOD 5 |
| 35 | 526.89 | 528 | 2.943 | METHOD 5 |
| 36 | 561.34 | 562 | 3.082 | METHOD 5 |
| 37 | 510.44 | 510 | 1.524 | METHOD 2 |
| 38 | 528.43 | 528 | 1.538 | METHOD 2 |
| 39 | 547.95 | 548 | 1.656 | METHOD 2 |
| 40 | 602.82 | 604 | 1.743 | METHOD 2 |
| 41 | 514.40 | 514 | 1.664 | METHOD 2 |
| 42 | 546.42 | 546 | 1.605 | METHOD 2 |
| 43 | 531.50 | 532 | 1.603 | METHOD 2 |
| 44 | 545.96 | 546 | 1.580 | METHOD 2 |
| 45 | 563.95 | 564 | 1.599 | METHOD 2 |
| 46 | 490.02 | 490 | 4.567 | METHOD 3 |
| 47 | 486.06 | 486 | 4.772 | METHOD 3 |
| 48 | 508.01 | 508 | 4.656 | METHOD 3 |
| 49 | 529.96 | 530 | 3.599 | METHOD 5 |
| 50 | 579.97 | 580 | 2.980 | METHOD 5 |
| 51 | 530.86 | 530 | 1.620 | METHOD 2 |
| 52 | 530.86 | 532 | 1.550 | METHOD 2 |
| 53 | 583.29 | 584 | 1.652 | METHOD 2 |
| 54 | 530.86 | 530 | 1.639 | METHOD 2 |
| 55 | 497.95 | 498 | 1.625 | METHOD 2 |
| 56 | 526.89 | 528 | 1.447 | METHOD 2 |
| 57 | 512.87 | 512 | 2.811 | METHOD 5 |
| 58 | 565.30 | 566 | 2.983 | METHOD 5 |
| 59 | 530.86 | 530 | 2.882 | METHOD 5 |
| 60 | 530.86 | 530 | 2.891 | METHOD 5 |
| 61 | 475.99 | 476 | 3.497 | METHOD 5 |
| 62 | 496.41 | 496 | 1.544 | METHOD 2 |
| 63 | 472.03 | 472 | 3.436 | METHOD 5 |
| 64 | 582.40 | 582 | 1.576 | METHOD 2 |
| 65 | 542.00 | 542 | 1.584 | METHOD 2 |
| 66 | 486.98 | 487 | 1.382 | METHOD 2 |
| 67 | 530.86 | 532 | 1.605 | METHOD 2 |

TABLE I-continued

| | | | | |
|---|---|---|---|---|
| 68 | 580.86 | 580 | 1.669 | METHOD 2 |
| 69 | 497.95 | 498 | 1.526 | METHOD 2 |
| 70 | 514.40 | 514 | 1.641 | METHOD 2 |
| 71 | 526.89 | 526 | 1.626 | METHOD 2 |
| 72 | 564.41 | 564 | 2.992 | METHOD 5 |
| 73 | 564.41 | 564 | 2.957 | METHOD 5 |
| 74 | 564.41 | 564 | 2.983 | METHOD 5 |
| 75 | 523.42 | 523 | 2.859 | METHOD 5 |
| 76 | 528.93 | 528 | 2.952 | METHOD 5 |
| 77 | 612.93 | 612 | 1.708 | METHOD 2 |
| 78 | 493.98 | 494 | 1.485 | METHOD 2 |
| 79 | 526.89 | 528 | 1.632 | METHOD 2 |
| 80 | 510.44 | 510 | 1.610 | METHOD 2 |
| 81 | 479.96 | 480 | 1.491 | METHOD 2 |
| 82 | 547.95 | 548 | 1.621 | METHOD 2 |
| 83 | 497.95 | 498 | 1.513 | METHOD 2 |
| 84 | 497.95 | 498 | 1.474 | METHOD 2 |
| 85 | 492.45 | 492 | 1.514 | METHOD 2 |
| 86 | 475.99 | 476 | 2.678 | METHOD 5 |
| 87 | 510.44 | 510 | 2.769 | METHOD 5 |
| 88 | 542.00 | 542 | 2.841 | METHOD 5 |
| 89 | 542.89 | 544 | 1.547 | METHOD 2 |
| 90 | 542.00 | 542 | 2.929 | METHOD 5 |
| 91 | 508.45 | 508 | 1.476 | METHOD 2 |
| 92 | 491.99 | 492 | 2.787 | METHOD 5 |
| 93 | 509.98 | 510 | 2.816 | METHOD 5 |
| 94 | 526.44 | 526 | 2.891 | METHOD 5 |
| 95 | 472.03 | 472 | 1.598 | METHOD 2 |
| 96 | 488.03 | 488 | 1.550 | METHOD 2 |
| 97 | 526.00 | 526 | 1.567 | METHOD 2 |
| 98 | 475.99 | 476 | 1.434 | METHOD 2 |
| 99 | 488.03 | 488 | 1.460 | METHOD 2 |

C: Biological Examples

Efficacy Against *Haemonchus contortus* in Jirds

Compounds according to this invention (numbers refer to the compound number in Table 1) were tested in vivo using *Haemonchus contortus* in jirds (*Meriones unguiculatus*). The jirds were orally infected with approximately 750-3.000 third-stage larvae of *Haemonchus contortus*. Ten days after infection, the jirds in the treatment groups were treated once either orally or subcutaneously with compounds at a dose of 10 mg or 50 mg per kg bodyweight. Three days after treatment, the jirds were necropsied, and the larvae burden in the stomach was determined. During the study no side-effects in jirds were observed. The efficacy was defined as the reduction of the mean larvae count in the infected jirds of the treatment group in comparison to the infected jirds in an untreated control group (negative control).

a) The compounds with Nos 1, 2, 3, 4, 5, 12, 13, 17, 19, 22, 23, 26, 31, 32, 33, 36, 37 and 40 reduced the *Haemonchus contortus* count by at least 50% when administered orally at 50 mg/kg bw.

b) The compounds with Nos 10, 11, 14, 57, 15, 16, 18, 20, 21, 24, 25, 27, 28, 29, 30, 34 and 35 reduced the *Haemonchus contortus* count by at least 50% when administered subcutaneously at 50 mg/kg bw.

c) The compounds with Nos 43, 46, 49, 42, 50, 53, 58, 64, 65, 66, 68, 72, 73, 74, 76, 77, 81, 82, 85, 87, 90, 92, 93, 95, 98 and 99 reduced the *Haemonchus contortus* count by at least 50% when administered orally at 10 mg/kg.

d) The compounds with Nos 41, 44, 45, 48, 51, 54, 59, 62, 63, 67, 69, 70, 71, 75, 78, 79, 80, 83, 84, 86, 88, 89, 91, 94, 96 and 97 reduced the *Haemonchus contortus* count by at least 50% when administered subcutaneously at 10 mg/kg.

DEFINITIONS

The term "alkyl" (alone or in combination with another term(s)) means a straight- or branched-chain saturated hydrocarbyl substituent (i.e., a substituent containing only carbon and hydrogen) typically containing from 1 to about 20 carbon atoms, more typically from 1 to about 8 carbon atoms, and even more typically from 1 to about 4 carbon atoms. Examples of such substituents include methyl, ethyl, n-propyl, isopropyl, n-butyl, iso-butyl, sec-butyl, tert-butyl, pentyl, iso-amyl, hexyl, and octyl. The term "$C_1$-$C_4$-alkyl" includes methyl, ethyl, n-propyl, isopropyl, n-butyl, iso-butyl, sec-butyl and tert-butyl, typically preferred are methyl and ethyl, even more preferred is typically methyl.

The term "halogen" (alone or in combination with another term(s)) means a fluorine radical ("fluoro", which may be depicted as F), chlorine radical ("chloro", which may be depicted as Cl), bromine radical ("bromo", which may be depicted as Br), or iodine radical ("iodo", which may be depicted as I). Typically, fluoro or chloro is preferred.

When a chemical formula is used to describe a monovalent substituent, the dash on the left side of the formula indicates the portion of the substituent that has the free valence. To illustrate, benzene substituted with —C(O)—OH has the following structure:

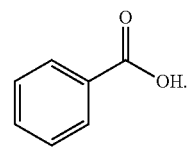

When a chemical formula is used to describe a di-valent (or "linking") component between two other components of a depicted chemical structure (the right and left components), the leftmost dash of the linking component indicates the portion of the linking component that is bound to the left component in the depicted structure. The rightmost dash, on the other hand, indicates the portion of the linking component that is bound to the right component in the depicted structure. In Formula (I) and compounds 8 and 10 the leftmost dash indicates the portion of Q which is bound to the nitrogen atom in the piperidine ring (Formula (I), 10) or halogen atom (8), and the rightmost dash indicates the portion of Q which is bound to the phenyl ring. Likewise in compounds 9, 11, 12 and 13 the leftmost dash indicates the portion of T which is bound to the CO-group (9, 11, 12) or CH$_2$OH-group (13), and the rightmost dash indicates the portion of T which is bound to the phenyl ring.

The term "pharmaceutically acceptable" is used adjectivally to mean that the modified noun is appropriate for use in a pharmaceutical product. When it is used, for example, to describe a salt, solvate, N-oxide, active compound or excipient, it characterizes the salt, solvate, N-oxide, active compound or excipient as being compatible with the other ingredients of the composition, and not deleterious to the intended recipient animal, e.g. to the extent that the benefit(s) outweigh(s) the deleterious effect(s).

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

The invention claimed is:

1. A method of treating a parasitic infection in an animal comprising administering to the animal a pharmaceutical composition comprising a compound selected from the group consisting of

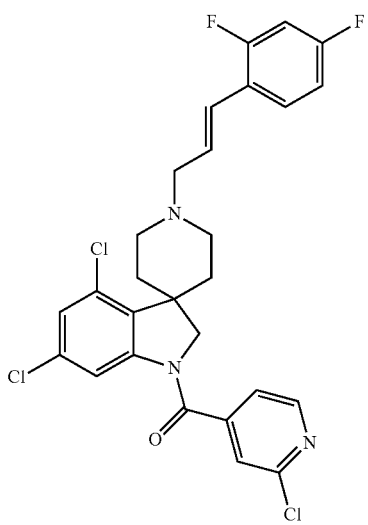

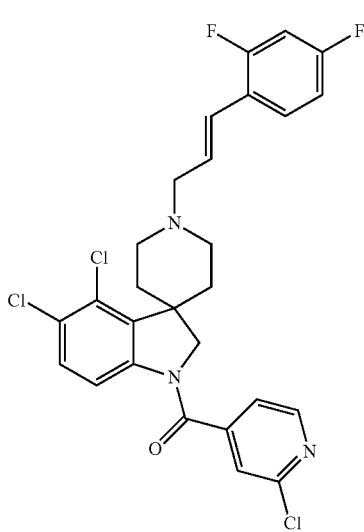

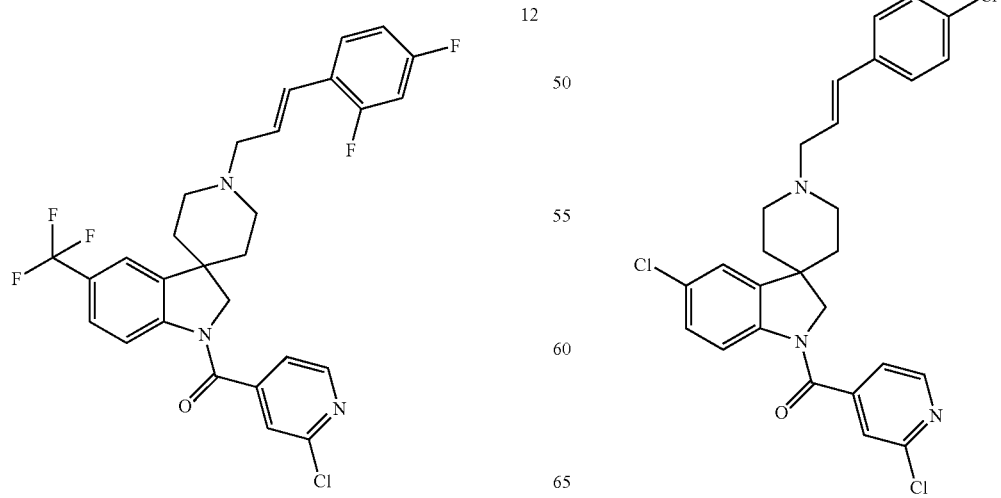

-continued

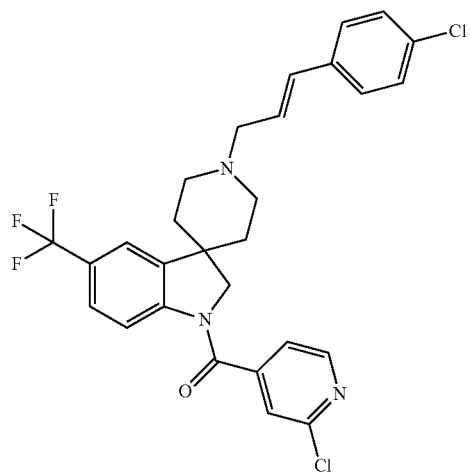
42

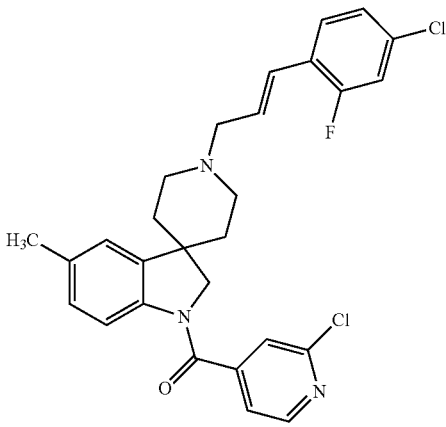
87 and pharmaceutically acceptable solvates, N-oxides and salts thereof.

2. The method of claim 1, wherein the pharmaceutical composition, further comprises one or more pharmaceutically acceptable excipients, and/or one or more pharmaceutically acceptable active ingredients which differ in structure from the compounds of claim 1.

3. The method of claim 1, wherein the helminth infection is a nematode infection.

4. The method as claimed in claim 1, wherein one or more of the parasites are resistant to one or more antiparasitic compounds.

5. The method of claim 1, wherein the animal is a non-human mammal.

6. The method of claim 1, wherein the pharmaceutical composition is administered orally.

7. The method of claim 1, wherein the pharmaceutical composition is administered parenterally.

8. The method of claim 1, wherein the compound selected from the group consisting of

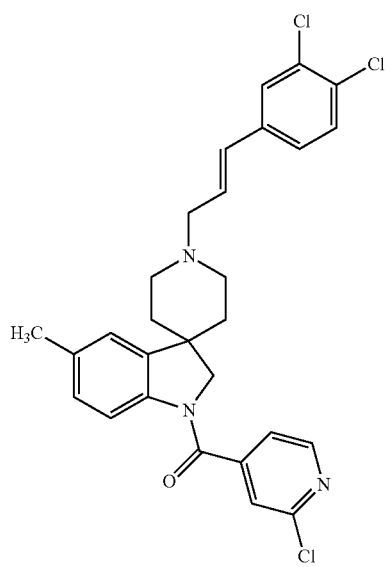
71

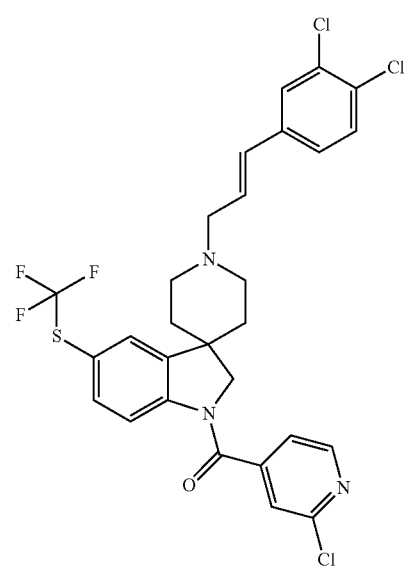
77

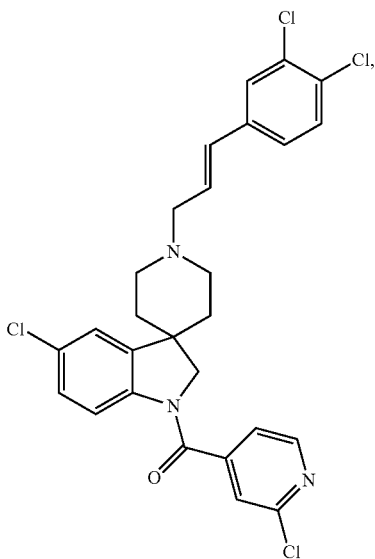
27

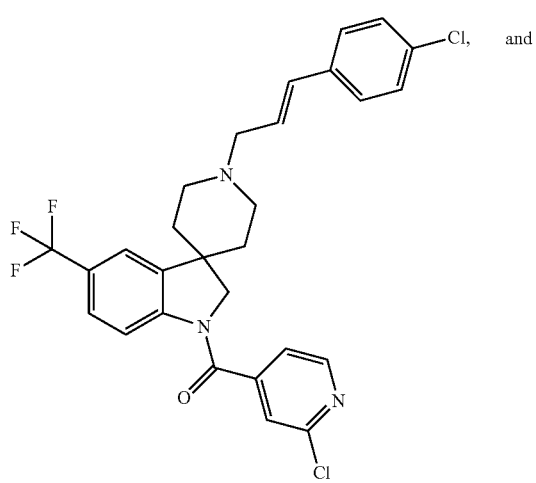
42
and
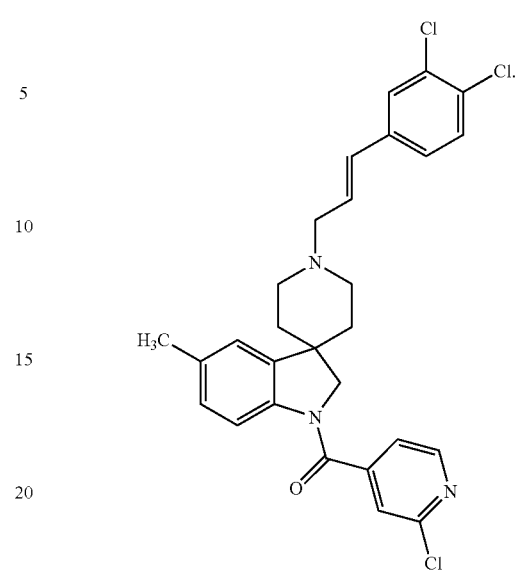
71
* * * * *